United States Patent
Liberatore et al.

(10) Patent No.: US 6,777,408 B1
(45) Date of Patent: Aug. 17, 2004

(54) PYRIDO-THIENO-DIAZEPINES METHOD FOR THE PRODUCTION THEREOF AND PHARMACEUTICAL COMPOSITIONS CONTAINING SAID PYRIDO-THIENO-DIAZEPINES

(75) Inventors: Anne-Marie Liberatore, Auffargis (FR); Dennis Bigg, Gif-sur-Yvette (FR)

(73) Assignee: Societe de Conseils de Recherches et d'Applications Scientifiques (S.C.R.A.S.) (FR)

(*) Notice: Subject to any disclaimer, the term of this patent is extended or adjusted under 35 U.S.C. 154(b) by 0 days.

(21) Appl. No.: 09/958,168

(22) PCT Filed: Apr. 7, 2000

(86) PCT No.: PCT/FR00/00881

§ 371 (c)(1),
(2), (4) Date: Oct. 4, 2001

(87) PCT Pub. No.: WO00/61587

PCT Pub. Date: Oct. 19, 2000

(30) Foreign Application Priority Data

Apr. 9, 1999 (FR) .............................. 99/04440

(51) Int. Cl.$^7$ ............................ A61K 31/55; A61P 5/00; C07D 495/14
(52) U.S. Cl. ........................................ 514/220; 540/495
(58) Field of Search ........................... 514/220; 540/495

(56) References Cited

FOREIGN PATENT DOCUMENTS

GB          2242427          10/1991

OTHER PUBLICATIONS

Yang, NOn–peptide Somatostatin Receptor Ligands, Annual Reports in Medicinal Chemistry, vol. 34, pp. 209–218, 1999.*

* cited by examiner

*Primary Examiner*—Brenda Coleman
(74) *Attorney, Agent, or Firm*—Muserlian, Lucas and Mercanti

(57) ABSTRACT

The present invention relates to novel pyrido-thieno-diazepines, their preparation process and the pharmaceutical compositions containing them. These diazepines are particularly useful for treating pathological states or diseases in which one (or more) somatostatin receptors are involved

18 Claims, No Drawings

PYRIDO-THIENO-DIAZEPINES METHOD FOR THE PRODUCTION THEREOF AND PHARMACEUTICAL COMPOSITIONS CONTAINING SAID PYRIDO-THIENO-DIAZEPINES

This application is a 371 of PCT/FR00/00881 filed Apr. 7, 2000.

The present invention relates to novel pyrido-thieno-diazepines, their preparation process and the pharmaceutical compositions containing them. These diazepines are particularly useful for treating pathological states or diseases in which one (or more) somatostatin receptors are involved.

Somatostatin (SST) was isolated for the first time as a factor inhibiting the secretion of growth hormone (Brazeau P. et al., Science 1973, 179, 77–79). This substance is known in two forms somatostatin 14 and somatostatin 28 and is widely distributed in the animal kingdom and in man. The peptides of this family also operate as neurotransmitters in the brain (hypothalamus, sensitive neurons, cerebral cortex) (Reisine T. et al., Neuroscience 1995, 67, 777–790; Reisine et al., Endocrinology 1995, 16:427–442) and in the endocrine organs (pancreas, intestine, kidney, salivary glands, thyroid C cells etc.). The bioactivity of somatostatin depends directly on a family of five recently cloned receptors.

Among the pathological disorders associated with somatostatin (Moreau J. P. et al., Life Sciences 1987, 40, 419; Harris A. G. et al., The European Journal of Medicine, 1993, 2, 97–105), there can be mentioned for example: acromgalia, hypophyseal adenomas which do not secrete growth hormones, hypophyseal adenomas which secrete thyreostimulin, Cushing's disease, gonadotrophinomas and prolactinomas, catabolic side-effects of glucocorticoids, hypophyseal adenomas without endocrinic action, insulin dependent diabetes, diabetic retinopathy, diabetic nephropathy, hyperthyroidism, gigantism, endocrinic gastoenteropancreatic tumors including carcinoid syndrome, VIPoma, insulinoma, nesidioblastoma, hyperinsulinemia, glucagonoma, gastrinoma and Zollinger-Ellison's syndrome, GRFoma as well as acute bleeding of the esophageal varices, gastroesophageal reflux, gastroduodenal reflux, pancreatitis, enterocutaneous and pancreatic fistulae but also diarrheas, refractory diarrheas of acquired immunodepression syndrome, chronic secretary diarrhea, diarrhea associated with irritable bowel syndrome, disorders linked with gastrin releasing peptide, secondary pathologies with intestinal grafts, portal hypertension as well as hemorrhages of the varices in patients with cirrhosis, gastrointestinal hemorrhage, hemorrhage of the gastroduodenal ulcer, Crohn's disease, systemic scleroses, dumping syndrome, small intestine syndrome, hypotension, scleroderma and medullar thyroid carcinoma, illnesses linked with cell hyperproliferation such as cancers and more particularly breast cancer, prostate cancer, thyroid cancer as well as pancreatic cancer and colorectal cancer, fibroses and more particularly fibrosis of the kidney, fibrosis of the liver, fibrosis of the lung, fibrosis of the skin, also fibrosis of the central nervous system as well as that of the nose and fibrosis induced by chemotherapy, and other therapeutic fields such as, for example, cephaleas including cephalea associated with hypophyseal tumors, pain, panic attacks, chemotherapy, cicatrization of wounds, renal insufficiency resulting from delayed development, obesity and delayed development linked with obesity, delayed uterine development, dysplasia of the skeleton, Noonan's syndrome, sleep apnea syndrome, Graves' disease, polycystic disease of the ovaries, pancreatic pseudocysts and ascites, leukemia, meningioma, cancerous cachexia, inhibition of H pylori, psoriasis, osteoporosis as well as Alzheimer's disease.

These diazepines have an affinity and a selectivity for the somatostatin receptors. The clinical applications of natural somatostatin and its peptide analogues are often limited. In fact, a poor bioavailability by oral route and low selectivity are often the main cause (Robinson, C., Drugs of the Future, 1994, 19, 992; Reubi, J. C. et al., TIPS, 1995, 16, 110). Due to their non peptide structure, the compounds of the present invention, agonists or antagonists of somatostatin, appear less susceptible to metabolic degradation than the. natural hormone and its peptide analogues and would thus have a superior duration of action. These compounds can be advantageously used for treating pathological states or the diseases as presented above and in which one (or more) somatostatin receptors are involved.

A subject of the present invention is therefore the compounds of general formula I

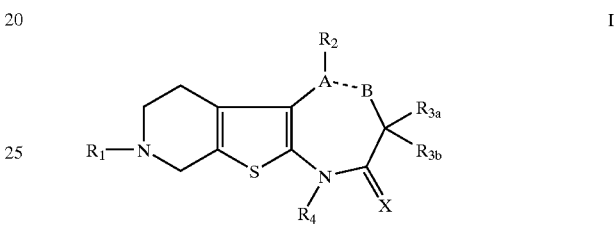

I under racemic, or enantiomeric or diastereoisomeric form or mixture thereof, and in which $R_1$ represents the hydrogen atom or a radical of formula $R'_1$—NH—C(Y)—;

$R'_1$ represents an aryl or heteroaryl radical, the aryl and heteroaryl radicals being optionally substituted;

$R_2$ represents a lower alkyl, trifluoromethyl radical or the phenyl radical optionally substituted;

X and Y represent independently O or S;

$R_{3a}$ represents the hydrogen atom, a lower alkyl, hydroxy radical or the radical of formula —OC(O) $R'_{3a}$;

$R'_{3a}$ represents an alkyl radical containing 1 to 10 carbon atoms optionally substituted;

$R_{3b}$ represents the hydrogen atom or a lower alkyl radical;

$R_4$ represents a radical of formula —$(CH_2)_n$—$CHR'_4R''_4$;

n represents the values 0, 1, 2, 3, 4, 5 or 6;

$R'_4$ and $R''_4$ represent, independently, the hydrogen atom, a lower alkyl, cycloalkyl, lower cycloaklyl alkyl aryl, lower arylalkyl, beteroaryl, lower heteroarylalkyl, arylcarbonyl or adamantyl, radical, these radicals being optionally substituted;

A—B represents —C=N— or —C—N($R_5$)—;

$R_5$ represents the hydrogen atom, a lower alkyl, lower alkenyl radical or a radical of formula —C(O)—$(CH_2)_p$—$R'_5$;

$R'_5$ represents the hydrogen atom, the radical amino, lower alkyl amino, di(lower alkyl)amino, cycloalkyl, heterocycloalkyl, guanidyl optionally susbtituted by nitro or cyano, aryl optionally substituted, heteroaryl or a radical of formula —NH—C(O)—$(CH_2)_c$—NH—C(O)—$(CH_2)_d$—$NH_2$;

p represents the values 0, 1, 2, 3, 4, 5, 6, 7, 8, 9 or 10;

c and d represent independently the values 0, 1, 2 or 3;

or a salt of these compounds.

A more particular subject of the invention is the compounds of general formula I as defined above in which the substituents, identical or different, of the aryl or heteroaryl radical represented by $R'_1$, are chosen from the following radicals: lower alkyl, lower alkoxy, lower alkylthio, lower alkoxy carbonyl, lower alkyl sulphonyl, halo, trifluoromethyl, trifluoromethyloxy, hydroxy, nitro, cyano, aryl, aryloxy, cycloalkyl or heterocycloalkyl;

the substituents, identical or different, of the phenyl radical represented by $R_2$, are chosen from: the hydroxy, halo radical, a lower alkyl or lower alkoxy radical;

the substituents, identical or different, of the alkyl radical represented by $R'_{3a}$, are chosen from the following radicals: cycloalkyl; heterocycloalkyl; aryl; heteroaryl; guanidyl optionally substituted by nitro or cyano; a radical of formula $NR''_{3a}R'''_{3a}$ in which $R''_{3a}$ and $R'''_{3a}$ represent, independently, the hydrogen atom, a lower alkyl, aryl, lower arylalkyl, lower heteroarylalkyl, alkylcarbonyl or alkoxycarbonyl radical;

the susbtitents, identical or different, of alkyl, cycloalkyl, cycloalkyl alkyl, aryl, arylalkyl, heteroaryl, heteroarylalkyl, arylcarbonyl or adamantyl radical represented independently by $R'_4$ and $R''_4$, are chosen from: the hydroxy, halo, trifluoromethyl radical, a lower alkyl or lower alkoxy radical;

the substituents, identical or different, of aryl represented by $R'_5$, are chosen from the following radicals: alkyl or alkoxyalkyl, these radicals alkyl or alkoxyalkyl being optionally substituted by oxy and amino.

In the definitions indicated above, the expression halo represents the fluoro, chloro, bromo or iodo radical, preferably chloro, fluoro or bromo. The expression lower alkyl preferably represents an alkyl radical having 1 to 6 carbon atoms, linear or branched, and in particular an alkyl radical having 1 to 4 carbon atoms such as the methyl, ethyl, propyl, isopropyl, butyl, isobutyl, sec-butyl and tert-butyl radicals, but can also represent a pentyl, isopentyl, hexyl or isohexyl radical.

The lower alkoxy radicals can correspond to the alkyl radicals indicated above such as for example the methoxy, ethoxy, propyloxy or isopropyloxy radicals but also linear, secondary or tertiary butoxy. The terrn lower alkylthio preferably designates the radicals in which the alkyl radical is as defined above such as for example methylthio, ethylthio. The term lower alkenyl preferably designates the alkenyl radical having 1 to 6 carbon atoms such as for example vinyl, allyl, butenyl. The term alkoxyallyl preferably designates the radical in which the alkoxy and alkyl radicals are as defined above.

The term cycloalkyl preferably designates the cyclopropyl, cyclobutyl, cyclopentyl or cyclohexyl rings. The expression heterocycloalkyl designates a saturated cycloalkyl containing 2 to 7 carbon atoms and at least one heteroatom. This radical can contain several identical or different heteroatoms. Preferably, the heteroatoms are chosen from oxygen, sulphur or nitrogen. As examples of heterocycloalkyl, the following can be mentioned: the pyrrolidine, imidazolidine, pyrrazolidine, isothiazolidine, thiazolidine, isoxazolidine, oxazolidine, piperidine, piperazine or morpholine ring.

The expression aryl represents an aromatic radical, constituted by a ring or condensed rings, such as for example the phenyl or naphthyl radical. The term aryloxy preferably designates the radicals in which the aryl radical is as defined above such as for example the phenoxy radical. The expression heteroaryl designates an aromatic radical, constituted by a ring or condensed rings, with at least one ring containing one or more identical or different heteroatoms chosen from sulphur, nitrogen or oxygem As an example of a heteroaryl radical the following radicals can be mentioned: thienyl, furyl, pyrrolyl, imidazolyl, pyrazolyl, isothiazolyl, thiazolyl, isoxazolyl, oxazolyl, pyridyl, pyrazinyl, pyrimidyl, benzothienyl, benzofuryl and indolyl.

The lower arylalkyl radicals designate the radicals in which respectively the aryl and lower alkyl radicals are as defined above such as for example benzyl, phenethyl or naphthylmethyl. The lower heteroarylalkyl radicals designate the radicals in which respectively the heteroaryl and lower alkyl radicals are as defined above such as for example indolylmethyl, thienylmethyl, fiirylmethyl. The termlower cycloalkyl alkyl designates the radicals in which respectively the cycloalkyl and lower alkyl radicals are as defined above.

The term alkylsulphonyl preferably designates the radicals in which the alkyl radical is as defined above. Similarly, the term arylcarbonyl, alkoxycarbonyl and alkylcarbonyl preferably designate the radicals in which the aryl, alkoxy and alkyl radicals are as defined above. The terms lower alkyl amino and di(lower alkyl) amino preferably designate the radicals in which the radicals alkyl are as defined above such as for example methylamino, ethylamino, dimethylamino, diethylamino or (methyl)(ethyl)amino.

According to the definition of the variable groups, a compound of formula I as defined above can have one or more asymmetrical carbons. The invention relates to the compounds of formula I as defined above, which compounds can be found in racemic, enantiomeric or diastereoisomeric form or a mixture thereof.

A more particular subject of the invention is the compounds of general formula I as defined above in which $R'_1$ represents an aryl radical optionally substituted by one or more substituents, identical or different, chosen from the following radicals: lower alkoxy, trifluoromethyl or nitro;

$R_2$ represents a lower alkyl radical or the radical phenyl optionally substituted by one or more groups, identical or different, chosen from halo or lower alkyl;

$R_{3a}$ represents the hydrogen atom, hydroxy or the radical of formula $-C(O)R'_{3a}$;

$R'_{3a}$ represents a linear or branched alkyl containing 1 to 6 carbon atoms optionally substituted by one or more substituents, identical or different, of formula $NR''_{3a}R'''_{3a}$ in which $R''_{3a}$ and $R'''_{3a}$ represent, independently, the hydrogen atom, a lower alkyl or alkoxycarbonyl.

$R_{3b}$ represents the hydrogen atom;

$R'_4$ and $R''_4$ represent, independently, the hydrogen atom, a lower alkyl, cycloalkyl, aryl, heteroaryl, arylcarbonyl or adamantyl radical;

A—B represents —C=N, and in a preferred manner, $R'_1$ represents a phenyl radical optionally substituted by one or more substituents, identical or different, chosen from the following radicals: lower alkoxy, tifluoromethyl or nitro;

$R_2$ represents a lower alkyl radical or the phenyl radical optionally substituted by one or more groups, identical or different, chosen from: methyl, chloro or fluoro;

$R'_{3a}$ represents a linear or branched alkyl containing 1 to 6 carbon atoms optionally substituted by one or more amino groups;

$R'_4$ and $R''_4$ represent, independently, the hydrogen atom, lower alkyl, cyclohexyl, phenyl, pyridyl, phenylcarbonyl or adamantyl;

More particularly, a subject of the invention is the compounds described hereafter in the examples and in which A—B represents —C=N—, in particular the compounds in which the $R_1$; $R'_1$; Y; $R_2$; $R_{3a}$; $R_{3b}$; X; n; $R'_4$; $R''_4$ radicals respectively have the following meanings:

H;-;-; 2-Cl-Phe; H; H; O; 1; H; Phe;
H;-;-; 2-Cl-Phe; H; H; S; 1; H; Phe;
H;-;-; 2-Cl-Phe; H; H; O; 2; H; Phe;
H;-;-; 2-Cl-Phe; H; H; O; 0; H; phenylcarbonyl;
H;-;-; 2-Cl-Phe; H; H; O; 0; H; Phe;
H;-;-; 2-Cl-Phe; H; H; O; 0; H; cyclohexyl;
H;-;-; 2-Cl-Phe; H; H; O; 4; H; H;
H;-;-; 2-Cl-Phe; H; H; O; 2; Phe; Phe;
H;-;-; 2-Cl-Phe; H; H; O; 2; Me; Me;
H;-;-; 2-Cl-Phe; H; H; O; 0; H; adamantyl;
H;-;-; 2-Cl-Phe; H; H; O; 1; H; pyridyl;
H;-;-; Phe; H; H; O; 1; H; Phe;
H;-;-; 4-Cl-Phe; H; H; O; 1; H; Phe;
H;-;-; 2-F-Phe; H; H; O; 1; H; Phe;
H;-;-; 4-F-Phe; H; H; O; 1; H; Phe;
H;-;-; 2-Me-Phe; H; H; O; 1; H; Phe;
H;-;-; t-butyl; H; H; O; 1; H; Phe;
H;-;-; 2-Cl-Phe; OH; H; O; 1; H; Phe;
H;-;-; 2-Cl-Phe; OC(O)—$(CH_2)_6NH_2$; H; O; 1; H; Phe;
$R'_1$—NH—C(Y)—; 2-$NO_2$-4-MeO-Phe; S; 2-Cl-Phe; H; H; O; 1; H; Phe;
$R'_1$—NH—C(Y)—; 2-$NO_2$-4-MeO-Phe; S; 2-Cl-Phe; H; H; O; 2; H; Phe;
$R'_1$—NH—C(Y)—; 2-$NO_2$-4-MeO-Phe; S; 2-Cl-Phe; H; H; S; 1; H; Phe;
$R'_1$—NH—C(Y)—; 2-$NO_2$-4-MeO-Phe; S; 2-Cl-Phe; H; H; O; 0; H; phenylcarbonyl;
$R'_1$—NH—C(Y)—; 2-$NO_2$-4-MeO-Phe; S; 2-Cl-Phe; H; H; O; 0; H; Phe;
$R'_1$—NH—C(Y)—; 2-$NO_2$-4-MeO-Phe; S; 2-Cl-Phe; H; H; O; 4; H; H;
$R'_1$—NH—C(Y)—; 2-$NO_2$-4-MeO-Phe; S; 2-Cl-Phe; H; H; O; 0; H; cyclohexyl;
$R'_1$—NH—C(Y)—; 2-$NO_2$-4-MeO-Phe; S; 2-Cl-Phe; H; H; O; 2; Phe; Phe;
$R'_1$—NH—C(Y)—; 2-$NO_2$-4-MeO-Phe; S; 2-Cl-Phe; H; H; O; 2; Me; Me;
$R'_1$—NH—C(Y)—; 2-$NO_2$-4-MeO-Phe; S; 2-Cl-Phe; H; H; O; 0; H; adamantyl;
$R'_1$—NH—C(Y)—; 2-$NO_2$-4-MeO-Phe; S; 2-Cl-Phe; H; H; O; 1; H; pyridyl;
$R'_1$—NH—C(Y)—; 2-$NO_2$-4-MeO-Phe; S; Phe; H; H; O; 1; H; Phe;
$R'_1$—NH—C(Y)—; 2-$NO_2$-4-MeO-Phe; S; 4-Cl-Phe; H; H; O; 1; H; Phe;
$R'_1$—NH—C(Y)—; 2-$NO_2$-4-MeO-Phe; S; 2-F-Phe; H; H; O; 1; H; Phe;
$R'_1$—NH—C(Y)—; 2-$NO_2$-4-MeO-Phe; S; 4-F-Phe; H; H; O; 1; H; Phe;
$R'_1$—NH—C(Y)—; 2-$F_3$C-Phe; O; 4-F-Phe; H; H; O; 1; H; Phe;
$R'_1$—NH—C(Y)—; 2-$NO_2$-4-MeO-Phe; S; 2-Me-Phe; H; H; O; 1; H; Phe;
$R'_1$—NH—C(Y)—; 2-$NO_2$-4-MeO-Phe; S; t-butyl; H; H; O; 1; H; Phe;
$R'_1$—NH—C(Y)—; 2-$NO_2$-4-MeO-Phe; S; 2-Cl-Phe; OH; H; O; 1; H; Phe;
$R'_1$—NH—C(Y)—; 2-$NO_2$-4-MeO-Phe; S; 2-Cl-Phe; —OC(O)—$(CH_2)_6NH_2$; H; O; 1; H; Phe;

A more particular subject of the invention is the compounds of general formula I as defined above in which $R'_1$ represents an aryl radical optionally substituted by one or more substituents, identical or different, chosen from the following radicals: lower alkoxy or nitro;

$R_2$ represents a phenyl radical optionally substituted by one or more identical or different halo groups;

$R_{3a}$ and $R_{3b}$ represent the hydrogen atom;

$R'_4$ and $R''_4$ represent, independently, the hydrogen atom, a lower alkyl or aryl radical;

A—B represents —C—N($R_5$)—;

$R_5$ represents the hydrogen atom, a lower alkenyl radical or a radical of formula —C(O)—$(CH_2)_p$—$R'_5$;

and in a preferred manner, $R'_1$ represents a phenyl radical optionally substituted by one or more substituents, identical or different, chosen from the following radicals: lower alkoxy or nitro;

$R_2$ represents a lower alkyl or phenyl radical optionally substituted by a chloro group;

$R'_4$ and $R''_4$ represent, independently, the hydrogen atom, lower alkyl or phenyl;

$R_5$ represents the hydrogen atom, pentenyl or a radical of formula —C(O)—$R'_5$;

$R'_5$ represents the hydrogen atom, a radical amino, cyclopentyle, indolyle, of formula —NH—C(O)—$CH_2$—NH—C(O)—$CH_2$—$NH_2$, or phenyl optionally substituted by one or more substituents, identical or different, chosen from alkyl and alkoxyalkyl radicals, these radicals alkyl and alkoxyalkyl being optionally substituted by oxy and amino.

More particularly, a subject of the invention is the compounds described hereafter in the examples and in which A—B represents —C—N($R_5$), in particular the compounds in which the $R_1$; $R'_1$; Y; $R_2$; $R_{3a}$; $R_{3b}$; X; $R_5$; n; $R'_4$; $R''_4$ radicals respectively have the following meanings:

H;-;-; 2-Cl-Phe; H; H; H; O; 1; H; Phe;
H;-;-; 2-Cl-Phe; H; H; H; O; 2; Me; Me;
H;-;-; 2-Cl-Phe; H; H; —$CH_2CH=C(Me)_2$; O; 1; H; Phe;
H;-;-; 2-Cl-Phe; H; H; aminohexylcarbonyl; O; 1; H; Phe;
H;-;-; 2-Cl-Phe; H; H; aminopentylcarbonyl; O; 1; H; Phe;
H;-;-; 2-Cl-Phe; H; H; indolylmethylcarbonyl; O; 1; H; Phe;
H;-;-; 2-Cl-Phe; H; H; aminobutylcarbonyl; O; 1; H; Phe;
H;-;-; 2-Cl-Phe; H; H; propylcarbonyl; O; 1; H; Phe;
H;-;-; 2-Cl-Phe; H; H; cyclopentyl-methylcarbonyl; O; 1; H; Phe;
H;-;-; 2-Cl-Phe; H; H; phenyl-propylcarbonyl; O; 1; H; Phe;
H;-;-; 2-Cl-Phe; H; H; phenylethylcarbonyl; O; 1; H; Phe;
H;-;-; 2-Cl-Phe; H; H; 4-(L-alanoyloxymethyl)benzyl carbonyl; O; 1; H; Phe;
H;-;-; 2-Cl-Phe; H; H; 4-aminomethyl-phenylcarbonyl; O; 1; H; Phe;
H;-;-; Phe; H; H; $NH_2$—$CH_2$—C(O)—NH—$CH_2$—C(O)—NH—$CH_2$—C(O)—; O; 2; Me; Me;
H;-;-; neopentyl; H; H; aminohexylcarbonyl; O; 1; H; Phe;
H;-;-; isobutyl; H; H; aninohexylcarbonyl; O; 1; H; Phe;
H;-;-; isobutyl; H; H; H; O; 1; H; Phe;
$R'_1$—NH—C(Y)—; 2-$NO_2$-4-MeO-Phe; S; 2-Cl-Phe; H; H; H; O; 4; H; H;
$R'_1$—NH—C(Y)—; 2-$NO_2$-4-MeO-Phe; S; 2-Cl-Phe; H; H; —$CH_2CH=C(Me)_2$; O; 1; H; Phe;
$R'_1$—NH—C(Y)—; 2-$NO_2$-4-MeO-Phe; S; 2-Cl-Phe; H; H; aminohexylcarbonyl; O; 1; H; Phe;
$R'_1$—NH—C(Y)—; 2-$NO_2$-4-MeO-Phe; S; 2-Cl-Phe; H; H; propylcarbonyl; O; 1; H; Phe;
$R'_1$—NH—C(Y)—; 2-$NO_2$-4-MeO-Phe; S; 2-Cl-Phe; H; H; cyclopentyl-methylcarbonyl; O; 1; H; Phe;
$R'_1$—NH—C(Y)—; 2-$NO_2$-4-MeO-Phe; S; 2-Cl-Phe; H; H; phenyl-propylcarbonyl; O; 1; H; Phe;
$R'_1$—NH—C(Y)—; 2-$NO_2$-4-MeO-Phe; S; 2-Cl-Phe; H; H; phenylethylcarbonyl; O; 1; H; Phe;
$R'_1$—NH—C(Y)—; 2-$NO_2$-4-MeO-Phe; S; 2-Cl-Phe; H; H; arminobutylcarbonyl; O; 1; H; Phe;

R'₁—NH—C(Y)—; 2-NO₂-4-MeO-Phe; S; 2-Cl-Phe; H; H; indolylmethylcarbonyl; O; 1; H; Phe;

R'₁—NH—C(Y)—; 2-NO₂-4-MeO-Phe; S; 2-Cl-Phe; H; H; aminopentylcarbonyl; O; 1; H; Phe;

R'₁—NH—C(Y)—; 2-NO₂-4-MeO-Phe; S; Phe; H; H; NH₂—CH₂—C(O)NH—CH₂—C(O)—NH—CH₂—C(O)—; O; 2; Me; Me;

R'₁—NH—C(Y)—; 2-NO₂-4-MeO-Phe; S; Phe; H; H; aminohexylcarbonyl; O; 2; Me; Me;

R'₁—NH—C(Y)—; 2-NO₂-4-MeO-Phe; S; neopentyl; H; H; aminohexylcarbonyl; O; 1; H; Phe;

R'₁—NH—C(Y)—; 2-NO₂-4-MeO-Phe; S; isobutyl; H; H; aminohexylcarbonyl; O; 1; H; Phe.

A compound of formula (I) according to the invention and in which A—B represents C═N, R₁ the hydrogen atom and R₃ₐ the hydrogen atom or an alkyl radical, can be obtained by reacting a compound of formula (1)

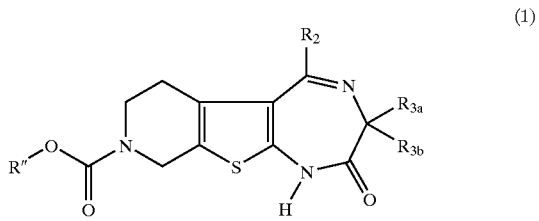

(1)

in which R₂, R₃ₐ R₃ᵦ have the meaning indicated above and R" represents a lower alkyl or lower arylalkyl radical, with a compound R₄Z in which R₄ has the meaning indicated above and Z represents a parting group, in the presence of a strong base, in order to obtain compound (2)

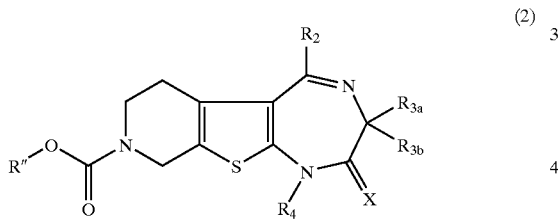

(2)

in which X represents the oxygen atom, compound (2) thus obtained which can be reacted with a thiation reagent in order to obtain compound (2) in which X represents a sulphur atom, compound (2) in which X represents an oxygen or sulphur atom, which is finally subjected to a deprotection reaction of the carbamate in order to obtain the desired product (I).

During the preparation of compounds (2) in which X represents the oxygen atom, the compounds of formula (1) are subjected to the action of a strong base such as for example sodium hydride in an inert solvent such as for example tetrahydrofuran or dimethylformamide at a temperature around 20° C. Compound R₄Z is then added to the reaction medium at a temperature around 20° C. then the reaction medium is heated to about 80° C. The parting group Z of compound R₄Z, can be for example a mesylate, tosylate or a halogen atom (preferably a chlorine or bromine atom). The preparation of compounds (2) in which X represents the sulphur atom starting from the compounds (2) in which X represents the oxygen atom, can be implemented at a temperature around 80° C. with a thiation agent such as phosphorus pentasulphide in a solvent such as pyridine.

The deprotection of the carbamate which does not affect the remainder of the molecule, can be carried out according to the known deprotection methods (T. W. Greene et al., Protective Groups in Organic Synthesis, Wiley-Interscience, 1991). Thus, in the case Iwhere R" represents a linear alkyl group (such as ethyl) or an arylalkyl group (such as benzyl), the deprotection of the carbamate can be implemented by agitating the reaction medium at ambient temperature in a strongly acid medium such as, for example, in the hydrobromic acid (33% in acetic acid). In the case where R" represents a more hindered alkyl group (such as t-butyl), the reaction can be implemented in the trifluoroacetic acid in an inert solvent such as dichloromethane at a temperature around 20° C.

The products of formula (1) can be prepared according to the method described in the Patent FR2645153 or according to similar methods.

Certain products of formula R₄Z are in general commercially available (for example from the firms Acros or Aldrich); the others can be prepared from the alcohol of formula R₄—OH in an inert solvent such as dichloromethane by the action for example of tosyl chloride in the presence of triethylamine or by the action of triphenylphosphine and carbon tetrabromide.

A compound of formula (I) according to the invention and in which A—B represents C═N, R₁ the hydrogen atom and R₃ₐ the hydroxy radical, can be obtained by oxidation of a compound of formula (2) as defined above, in an inert solvent in order to obtain a compound of formula (3)

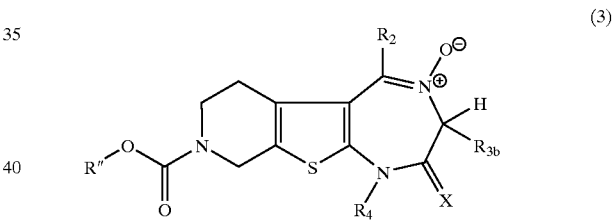

(3)

in which R₂, R₃ᵦ, R₄, R" and X have the meaning indicated above, which compound of formula (3) is treated with acetic anhydride in order to obtain a compound of formula (4)

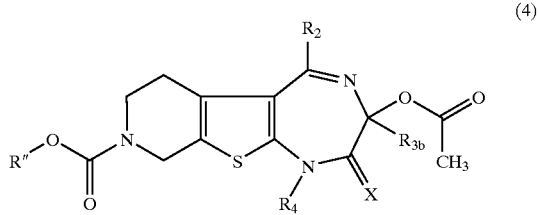

(4)

in which R₂, R₃ᵦ, R₄, R" and X have the meaning indicated above, which compound (4) is then saponified in order to obtain the compound of formula (5)

(5)

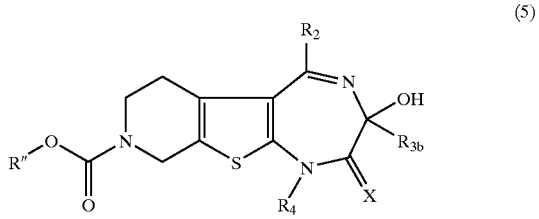

in which $R_2$, $R_{3b}$, $R_4$, R" and X have the meaning indicated above,
which compound (5) is finally subjected to a deprotection reaction of the carbamate in order to obtain the corresponding compound of formula (I) in which $R_1$ represents H and $R_{3a}$ the hydroxy radical.

The oxidation of compound (2) at the level of the jinine of the diazepine, can be carried out by the action of an organic oxidizing agent such as for example metachioroperoxybenzoic acid, at a temperature around 20° C., in an inert solvent such as dichloromethane or 1,2-dichloroethane. The reaction of compound (3) with acetic anhydride is a Polonowski type rearrangement (Gilman N. W. et al., J. Am. Chem. Soc. 1990, 112, 3969–3978) which can be implemented at a temperature around 70° C. The saponification reaction of compound (4) can be carried out by the action of a mineral base such as for example sodium hydroxide or lithium hydroxide, in a lower aliphatic alcohol (methanol, ethanol for example), at a temperature around 20° C.

A compound of formula (I) according to the invention and in which A—B represents C=N, $R_1$ the hydrogen atom and $R_{3a}$ an —OC(O)—$R'_{3a}$ radical, can be obtained by reacting a compound of formula (5) as defined above, with an acid of formula $R'_{3a}C(O)OH$ in which $R'_{3a}$ has the meaning indicated above, in order to obtain a compound of formula (6)

(6)

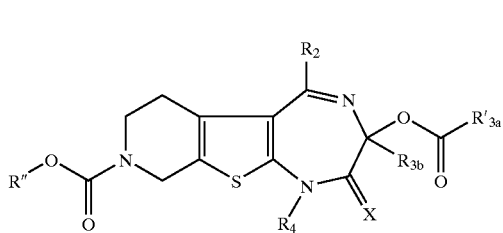

in which $R_2$, $R'_{3a}$, $R_{3b}$, $R_4$, R" and X have the meaning indicated above, which compound (6) is finally subjected to a deprotection reaction of the carbamate in order to obtain the corresponding compound of formula (I) in which $R_1$ represents H and $R_{3a}$ the —OC(O)$R'_{3a}$ radical.

The conversion of compound (5) into compound (6) can be carried out under conditions similar to those of esterification reactions, known to a person skilled in the art; thus it can be implemented at a temperature around 20° C. in an inert solvent such as dichloromethane or 1,2-dichloroethane.

The compounds of formula I according to the invention in which A—B represents C=N, $R_1$ a radical of formula $R'_1$—NH—C(Y)—, can be prepared according to the process which consists of reacting the corresponding compound of formula (I) in which $R_1$ represents the hydrogen atom, with a compound of formula $$R'_1-N=C=Y \quad (7)$$

in which $R'_1$ and Y have the meaning indicated above, in order to form the chosen compound of formula I.

During the preparation of the compound of formula I in which $R_1$ represents a radical of formula $R'_1$—NH—C(Y)—, the addition of the compound of formula (7), to the compound of formula (I) in which $R_1$ represents the hydrogen atom, is easily carried out at a temperature around 20° C. in a chlorinated solvent such as dichloromethane or 1,2-dichloroethane. The products of formula (7) are in the main commercially available or can be prepared by reacting the corresponding amine with (thio)phosgene according to methods known to a person skilled in the art.

A compound of formula (I) according to the invention and in which A—B represents —C—N($R_5$)—, $R_1$ and $R_5$ a hydrogen atom and $R_{3a}$ the hydrogen atom or an alkyl radical, can be obtained by the action of a gentle reducing agent in acid medium, on a compound of formula (2) as defined above, in order to obtain the compound of formula (8)

(8)

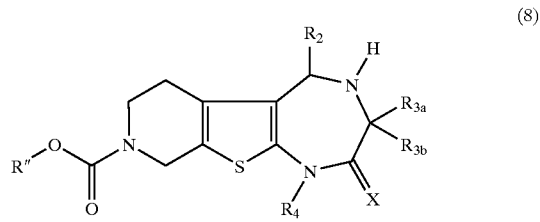

in which $R_2$, $R_{3a}$, $R_{3b}$, $R_4$, X and R" have the meaning indicated above, which compound (8) is subjected to a deprotection reaction of the carbamate in order to obtain the desired product (I) in which $R_1$ represents the hydrogen atom.

During the reduction of compound (2) to obtain compound (8), a gentle reducing agent can be used such as sodium cyanoborohydride in a solvent such as a lower alcoholic solvent (methanol, ethanol for example) at a temperature around 20° C.

A compound of formula (1) according to the invention and in which A—B represents C—$NR_5$, $R_1$ represents a hydrogen atom, $R_{3a}$ the hydrogen atom or the alkyl radicals and $R_5$ represents a alkenyl radical, can be obtained by reacting a compound of formula (8) as defined above, with a compound of formula $Z'R_5$ in which $R_5$ has the meaning indicated above and $Z'$ represents a parting group, in the presence of a strong mineral base in an inert solvent, in order to obtain compound (9)

(9)

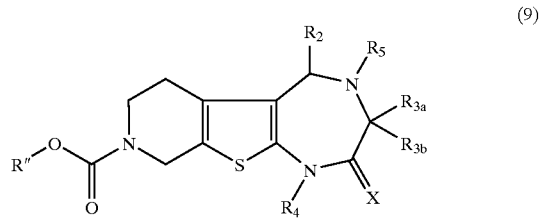

in which $R_2$, $R_{3a}$, $R_{3b}$, $R_4$, X, R" and $R_5$ have the meaning indicated above,
which compound (9) is subjected to a deprotection reaction of the carbamate in order to obtain the desired product (I) in which $R_1$ represents the hydrogen atom.

The preparation of compound (9) starting from compound (8), can be implemented by the action of sodium hydride in a solvent such as tetrahydrofuran at a temperature around 60° C. The parting group $Z'$ of compound $Z'R_5$ can be a mesylate, tosylate or a halogen atom.

A compound of formula (1) according to the invention and in which A—B represents —C—N($R_5$)—, $R_1$ represents a hydrogen atom, $R_{3a}$ the hydrogen atom or the alkyl radical and $R_5$ represents an —C(O)—(CH)$_p$—R'$_5$ radical, can be obtained by reacting a compound of formula (8) as defined above, with an acid of formula R'$_5$—(CH$_2$)$_p$—C(O)OH in which R'$_5$ and p have the meaning indicated above, in order to obtain the corresponding compound (10),

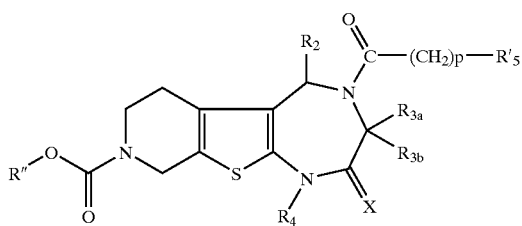

(10)

in which $R_2$, $R_{3a}$, $R_{3b}$, $R_4$, X, R", p and R'$_5$ have the meaning indicated above, which compound (10) is subjected to a deprotection reaction of the carbamate in order to obtain the desired product (I) in which $R_1$ represents the hydrogen atom.

The reaction of compound R'$_5$—(CH$_2$)$_p$—C(O)OH with compound (8) can be carried out under conditions similar to peptide coupling reactions. It can be implemented at a temperature around 20° C. in an inert solvent such as dichloromethane or 1,2-dichloroethane.

A compound of formula (I) according to the invention and in which A—B represents —C—N($R_5$)—, $R_1$ the hydrogen atom and $R_{3a}$ the hydroxy radical, can be obtained by reduction of the compound of formula (4), in order to obtain the compound of formula (11)

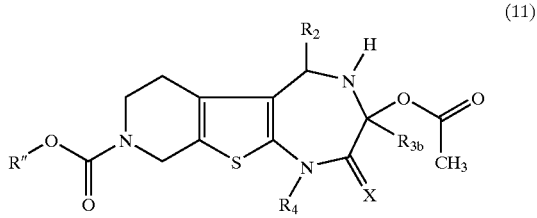

(11)

in which $R_2$, $R_{3b}$, $R_4$, X and R" have the meaning indicated above, which compound (11) is either subjected to a saponification reaction then to a deprotection reaction of the carbamate in order to obtain the desired product (I) in which $R_1$ and $R_5$ represent the hydrogen atom;

or treated with a compound of formula halo-$R_5$ in which $R_5$ represents an alkenyl radical or an acid of formula R'$_5$—(CH$_2$)$_p$—C(O)OH in which R'$_5$ and p have the meaning indicated above, in order to obtain the compound of formula (12)

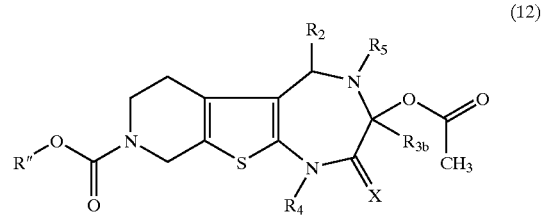

(12)

in which $R_2$, $R_{3b}$, $R_4$, X and R" have the meaning indicated above and $R_5$ represents respectively an alkenyl radical or R'$_5$CH$_2$)$_p$—C(O)—, which compound (12) is finally subjected to a saponification reaction then a deprotection reaction of the carbamate in order to obtain the desired product (I) in which $R_1$ represents the hydrogen atom and $R_5$ an alkenyl radical or R'$_5$—(CH$_2$)$_p$—C(O)—.

A compound of formula (I) according to the invention and in which A—B represents —C—N($R_5$)—, $R_1$ the hydrogen atom and $R_{3a}$ an —OC(O)—R'$_{3a}$ radical, can be obtained by reduction of the compound of formula (6), in order to obtain a compound of formula (13)

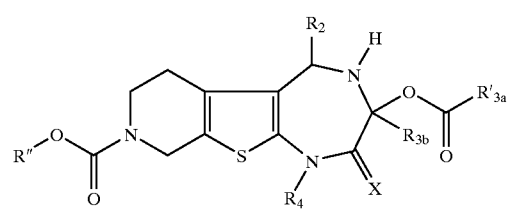

(13)

in which $R_2$, R'$_{3a}$, $R_{3b}$, $R_4$, X and R" have the meaning indicated above, which compound (13) is either subjected to a deprotection reaction of the carbamate in order to obtain the desired product (I) in which $R_1$ and $R_5$ represent the hydrogen atom;

or treated with a compound halo-$R_5$ in which $R_5$ represents an alkenyl radical or an acid of formula R'$_5$—(CH$_2$)$_p$—C(O)OH in which R'$_5$ and p have the meaning in indicated above, in order to obtain the compound of formula (14)

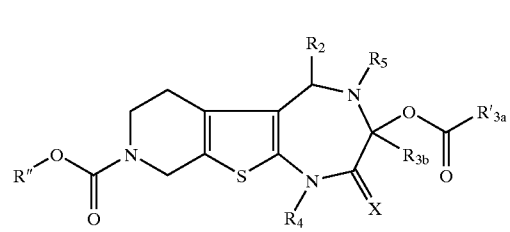

(14)

in which $R_2$, R'$_{3a}$, $R_{3b}$, $R_4$, X and R" have the meaning indicated above and $R_5$ represents respectively an alkenyl radical or R'$_5$—(CH$_2$)$_p$—C(O)—, which compound (14) is finally subjected to a deprotection reaction of the carbamate in order to obtain the desired product (I) in which $R_1$ represents the hydrogen atom and $R_5$ respectively an alkenyl radical or R'$_5$—(CH$_2$)$_p$—C(O)—.

The conditions for adding the radical $R_5$ (different firm H) to the nitrogen atom of diazepines (11) and (13) are identical to the reaction conditions for the preparation of compounds (9) and (10). The deprotection reactions of the carbamates (5), (6), (8), (9), (10), (13) and (14) are as defined previously; the R" radical is chosen according to the other fumctions present in the molecule and with the aim of obtaining a selective deprotection of the carbamate group R"OC(O)N—.

The compounds of formula I according to the invention in which A—B represents —C—N($R_5$)— and $R_1$ represents a radical of formula $R'_1$—NH—C(Y)—, can be prepared by the action of a compound of formula (7) $R'_1$—N=C=Y in which R', and Y have the meaning indicated above, on the corresponding compound of formula (I) in which $R_1$ represents the hydrogen atom, in order to form the chosen compound of formula I.

The compounds of formula (2) are new. A subject of the invention is also, as new industrial products, and in particular as new industrial products intended for the preparation of the compounds of formula (I) according to the invention, the products of formula (2).

The compounds I of the present invention have useful pharmacological properties. Thus it was discovered that the compounds I of the present invention have a high affinity for one (or more) of the somatostatin receptors. They can be used as non-peptide agonists or antagonists of somatostatin in a selective or non-selective manner.

The compounds of the present invention can therefore be used in different therapeutic applications. They can advantageously be used for treating the pathological states or diseases as presented above and in which one (or more) of the somatostatin receptors are involved.

An illustration of the pharmacological properties of the compounds of the invention will be found hereafter in the experimental part.

A subject of the present Application is also, as medicaments, the products of formula I as defined above, as well as the addition salts with pharmaceutically acceptable mineral or organic acids of said products of formula I, as well as the pharmaceutical compositions containing, as active ingredient, at least one of the medicaments as defined above, in combination with a pharmaceutically acceptable support The pharmaceutical composition can be in solid form, for example, powders, granules, tablets, gelatin capsules or suppositories. The appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound according to the invention can also be presented in liquid form such as, for example, solutions, emulsions, suspensions or syrups. The appropriate liquid supports can be, for example, water, organic solvents such as glycerol or glycols, similarly their mixtures, in varied proportions, in water, with phannaceutically acceptable oils or greases added to them. Sterile liquid compositions can be used for intramuscular, intaperitoneal or subcutaneous injections and sterile compositions can also be administered intravenously.

All the technical and scientific terms used in the present text have the meanings known to a person skilled in the art. Similarly, all patents (or patent applications) as well as other bibliographical references are incorporated by way of reference.

The following examples are presented to illustrate dte above procedures and must in no case be considered as a limit to the scope of the invention.

EXPERIMENTAL PART

Example 1

5-(2-chlorophenyl)-1,3,6,7,8,9-hexahydro-1-(2-phenylethyl)-2H-pyrido[4',3':4,5]thieno[2,3-e]-1,4-diazepine-2-one $1^{st}$ Stage ethyl 5-(2-chlorophenyl)-1,2,3,6,7,9-hexahydro-2-oxo-1-(2-phenylethyl)-8H-pyrido[4',3':4,5]thieno[2,3-e]-1,4-diazepine-8-carboxylate 18 g of ethyl 5-(2-chlorophenyl)-1,2,3,6,7,9-hexahydro-2-oxo-8H-pyrido[4',3':4,5]thieno[2,3-e]-1,4-diazepine-8-carboxylate (4.46 mmol) is solubilized under argon, in 180 ml of anhydrous dimethylformamide. Sodium hydride at 60% (1.784 g, 4.46 mmol) is added then the reaction medium is heated for approximately 30 minutes at 50° C. until there is no more release. The reaction medium is cooled down to a temperature around 20° C. then 2-bromoethylbenzene (6.2 ml, 4.46 mmol) is added with a syringe. Agitation is carried out for 16 hours at 23° C. then the reaction medium is poured into a saturated solution of ammonium chloride (400 ml). Extraction is carried out with ethyl acetate (2×500 ml). The organic phase is dried over magnesium sulphate then the solvent is evaporated off with a rotary evaporator. After purification by chromatography on a silica column (eluent ethyl acetate-heptane: 0-100 to 20-80), the fractions containing only the product are evaporated and the desired product is obtained in the form of a white amorphous powder (20.3 g, 89%).

Melting point: 70–78° C.

NMR $^1$H (400 MHz, $CDCl_3$, δ): 1.07 (m, 3H); 1.46 (m, 1H); 1.93–1.97 (m, 1H); 2.85 (m, 2H); 3.08 (m, 1H); 3.69 (m, 2H); 3.69 (m, 1H); 4.02 (m, 2H); 4.38 (m, 2H); 4,73 (m, 2H); 7.20–7.49 (m, 9H).

IR ($cm^{-1}$): 3427; 2978; 2927; 1686 (v C=O carbamate); 1678 (v lactame); 1231; 1115; 761.

$2^{nd}$ Stage 5-(2-chlorophenyl)-1,3,6,7,8,9-hexahydro-1-(2-phenylethyl)-2H-pyrido[4',3':4,5]thieno[2,3-e]-1,4-diazepine-2-one A mixture containing the compound obtained in the previous stage (20.3 g, 0.04 mol) in a solution of hydrobromic acid at 33% in the acetic acid (500 ml) is agitated for 12 hours at a temperature around 20° C. The reaction medium is heated for 3 hours at 40° C. then the acids are evaporated with a rotary evaporator. The oil obtained is taken up in 300 ml of water then a saturated solution in sodium bicarbonate (300 ml) is added slowly and with caution. Extraction is carried out with dichloromethane (2×300 ml), followed by drying over magnesium sulphate and the solvent is evaporated off in order to obtain the desired product in the form of a purplish-blue amorphous powder (17 g, 97%).

Melting point: 70–78° C.

IR ($cm^{-1}$): 3427; 2978; 2927; 1678 (v lactame); 1231; 1115; 761.

HPLC (UV): 99%

Example 2

5-2-chlorophenyl)-1,2,3,6,7,9-hexahydro-N-(4-methoxy-2-nitrophenyl)-2-oxo-1-(2phenyl-ethyl)-8H-pyrido[4',3':4,5]thieno[2,3-e]-1,4-daizepine-8-carbothioamide A mixture containing the 5-(2-chlorophenyl)-1,3,6,7,8,9-hexahydro-1-(2-phenylethyl)-2H-pyrido[4',3':4,5]thieno[2,3-e]-1,4-diazepine-2-one (0.2 g, 0.46 mmol) and 4-methoxy-2-nitroisothiocyanate (0.096 g, 0.46 mmol) in 4 ml of anhydrous dichloromethane is agitated for 3 hours at a temperature around 20° C. and under an argon atmosphere. Ether (2 ml) is added to the reaction medium and agitation is carried out for approximately thirty minutes until precipitation occurs. The solid is filtered on frit and washed with isopropyl ether (2×5 ml) then with isopentane (5 ml). After drying under vacuum at a temperature below 100° C., the desired product is obtained in the form of a yellow powder (0.195 g, 66%).

Melting point: 145–150° C.

NMR $^1$H (400 MHz, CDCl$_3$, δ); 1.70 (m, 1H); 2.12 (m, 1H); 2.81–2.88 (m, 2H); 3.55 (m, 1H); 3.74 (m, 1H); 3.84 (s, 3H); 3.96 (m, 1H); 4.23 (m, 1H); 4.41 (m, 1H); 4.73–4.82 (m, 2H); 5.42 (m, 1H); 7.20–7.51 (m, 12H); 9.49 (s, 1H).

IR (cm$^{-1}$): 3427; 2978; 2927; 1678 (ν C=O lactame); 1530; 1210; 1030.

HPLC (UV): 99%

Example 3

5-(2-chlorophenyl)-1,3,6,7,8,9-hexahydro-1-(2-phenylethyl)-2H-pyrido[4',3':4.5]thieno[2,3-e]-1,4-diazepine-2-thione 1$^{st}$ Stage ethyl 5-(2-chlorophenyl)-1,2,3,6,7,9-hexahydro-1-(2-phenylethyl)-2-thioxo-8H-pyrido[4',3':4,5]thieno[2,3-e]-1,4-diazepine-8-carboxylate A mixture containing the ethyl 5-(2-chlorophenyl)-1,2,3,6,7,9-hexahydro2-oxo-1-(2-phenylethyl)-8H-pyrido[4',3':4.5]thieno[2,3-e]-1,4-diazepine-8-carboxyl (0.97g, 1.91 mmol) and phosphorus pentasulphide (0.425 g, 1.91 mmol) in pyridine (10 ml) is heated at a temperature around 85° C. and for 5 hours. The temperature is returned to around 20° C. and the residue is filtered on frit. The pyridine contained in the filtrate is evaporated with a rotary evaporator (with the help of toluene). Then dichloromethane (40 ml) is added then the organic phase is washed, dried over magnesium sulphate and the solvent is evaporated off. Then the powder obtained is heated for one hour under reflux of acetonitrile (100 ml). After evaporation of the solvent with a rotary evaporator, purification is carried out by chromatography on a silica column (eluent: ethyl acetate-heptane: 20-80 to 45-55). The fractions containing only the product are evaporated in order to obtain the desired product in the form of a yellow powder (0.1 g).

NMR $^1$H (400 MHz, CDCl$_3$, δ); 0.84 (m, 3H); 1.49 (m, 1H); 1.95–1.99 (m, 1H); 2.8–3.12 (m, 3H); 3.70 (m, 2H); 4.03–4.19 (m, 2H); 4.31–4.34 (m, 2H); 4.80 (m, 1H); 4.98–5.05 (m, 1H); 5.37 (d, 1H); 6.95–7.67 (m, 9H).

IR (cm$^{-1}$): 3427; 2978; 2927; 1701 (ν C=O lactame); 1592; 1384; 1296; 1225; 761.

2$^{nd}$ Stage 5-(2-chlorophenyl)-1,3,6,7,8,9-hexahydro-1-(2-phenylethyl)-2H-pyrido[4',3':4,5]thieno[2,3-e]-1,4-diazepine-2-thione The compound obtained during the previous stage (0.1 g, 0.19 mmol) in hydrobromic acid diluted to 33% in acetic acid (30 ml) is agitated for three days. The acids are evaporated with a rotary evaporator with help of toluene. Dichlorometlane (30 ml) and a saturated solution of sodium bicarbanate (50 ml) are added Agitation is carried out for a few hours then the organic phase is extracted and dried over magnesium sulphate and the solvent is evaporated off in order to obtain the desired product.

Example 4

5-(2-chlorophenyl)-1,2,3,6,7,9-hexahydro-N-(4-methoxy-2-nitrophenyl)-1-(2-phenylethyl)-2-thioxo-8H-pyrido[4',3':4,5]thieno[2,3-e]-1,4-diazepine-8-carbothioamide 86 mg of 5-(2-chlorophenyl)-1,3,6,7,8,9-hexahydro-1-(2-phenylethyl)-2H-pyrido[4',3':4.5]thieno[2,3-e]-1,4-diazepine-2-thione is reacted with 4-methoxy-2-nitroisothiocyanate (0.040 g, 0.19 mmol) in 2 ml of dichloromethane at a temperature around 20° C. The reaction mixture is agitated for 2 hours and isopropyl ether (3 ml) is added until precipitation occurs. After filtration on frit and washing with isopropyl ether (2×3 ml) and with isopentane (5 ml), purification is carried out by chromatography on a silica column (eluent: ethyl acetate-heptane: 20-80 to 40-60). After evaporation of the fractions containing only the product, the desired product is obtained in the form of an orange powder (0.03 g, 24%).

Melting point: 152° C.

HPLC MS: 99% at 230 nm (MH+ found 662.1; MH+ theoretical 662.2)

Example 5

5-(2-chlorophenyl)-1,2,3,6,7,9-hexahydro-3-hydroxy-1-(2-phenylethyl)-8H-pyrido[4',3':4,5]thieno[2,3-e]-1,4-diazepine-2-one 1$^{st}$ Stage t-butyl 5-2-chlorophenyl)-1,2,3,6,7,9-hexahydro-4-oxide-2-oxo-1-(2-phenylethyl)-8H-pyrido[4',3':4,5]thieno[2,3-e]-1,4-diazepine-8-carboxylate t-butyl 5-(2-chlorophenyl)-1,2,3,6,7,9-hexahydro-2-oxo-1-(2-phenylethyl)-8H-pyrido[4',3':4.5]thieno[2,3-e]-1,4-diazepine-8-carboxylate (22 g, 41 mmol) is dissolved a 23° C. in 1,2-chloro ethane (320 ml). Meta-chloroperoxybenzoic acid at 85% (21.6 g, 0.1 mol) is added. Agitation is carried out for 24 hours at 23° C. then a solution of 5N sodium hydroxide (400 ml) is added. After decanting, the organic phase is washed with water, dried over magnesium sulphate, filtered and concentrated with a rotary evaporator. After purification by chromatography on a silica column (eluent: ethyl acetate-heptane: 50-50 to 80-20), the fractions containing only the product ae evaporated. The solid obtained is agitated in a mixture of solvents: isopropyl ether-isopentane (20-80). After filtration on frit and washing with isopentane, the desired product is obtained in the form of a white powder (5.9 g, 26%).

NMR $^1$H (400 MHz, CDCl$_3$, δ): 1.35 (s, 9H); 1.96 (m, 1H); 2.87–3.07 (m, 3H); 3.70 (m, 1H); 3.88 (m, 1H); 4.30 (m, 1H); 4.45 (m, 2H); 4.67 (m, 1H); 4.99 (m, 1H); 6.81 (s, 1H); 7.22–7.84 (m, 9H).

IR (cm$^{-1}$): 1689 (ν C=O carbamate); 1679 (ν C=O lactame); 750.

HPLC (UV): 99%

2$^{nd}$ Stage t-butyl 3-acetyloxy-5-2-chlorophenyl)-1,2,3,6,7,9-hexahydro-2-oxo-1-(2-phenylethyl)-8H-pyrido[4',3':4,5]thieno[2,3-e]-1,4-diazepine-8-carboxylate The compound obtained in the previous stage (5.8 g, 10 mmol) is poured into acetic anhydride (58 ml) then heated at 70° C. for 2 hours. The reaction medium is left to cool down then it is poured into a saturated solution of sodium bicarbonate at 10% (150 ml). Agitation is carried out for 30 minutes followed by extraction with ethyl acetate. After decanting, the organic phase is washed with a saturated solution of sodium bicarbonate at 10% (2×150 ml) then with water (2×150 ml). The organic phase is dried over magnesium sulphate and the solvent is evaporated off. After purification by chromatography on a silica column (eluent: ethyl acetate-heptane: 20-80 to 50-50), the fractions containing only the product are evaporated. The solid obtained is retreated in a mixture of solvents: isopropyl ether-isopentane (20-80). After filtration on frit and washing with isopentane, the desired product is obtained in the form of a beige powder (5.2 g, 84%).

IR (cm$^{-1}$): 3420; 2975; 1742 (ν C=O ester); 1702 (ν C=O carbamate); 1679 (ν lactame); 1233; 1111; 755.

3$^{rd}$ Stage t-butyl 5-(2-chlorophenyl)-1,2,3,6,7,9-hexahydro-3-hydroxy-2-oxo-1-(2-phenylethyl)-8H-pyrido[4',3':4,5]thieno[2,3-e]-1,4-diazepine-8-carboxylate The compound obtained in the previous stage (2.5 g, 4.2 mmol) is dissolved in methanol (60 ml). The reaction medium is cooled down to −5° C. then a solution of sodium hydroxide (0.168 g in 6 ml of water) is added dropwise. Agitation is carried out for 2 hours at 23° C. The solvent is evaporated off then the reaction mixture is taken up in dichloromethane, followed by washing with water then with a saturated solution of ammonium chloride (2×100 ml). After decanting, the organic phase is washed with water, dried over magnesium. sulphate and the solvent is evaporated off. After purification by chromatography on a silica column (eluent: ethyl acetate-heptane: 20-80 to 50-50), the fractions containing only the product are evaporated. After filtration on frit and washing with isopentane, the desired product is obtained in the form of a yellow powder (4.1 g, 87%).

Melting point: 138–140° C.

4$^{th}$ Stage 5-(2-chlorophenyl)-1,2,3,6,7,9-hexahydro-3-hydroxy-1 2-phenylethyl)-8H-pyrido[4',3':4,5]thieno[2,3-e]-1,4-diazepine-2-one The product obtained in the previous stage (0.56 g, 1 imnol) is solubilized in dichloromethane (8 ml). Trifluoroacetic acid (2.5 ml) is added and agitation is carried out for 2 hours at 23° C. The solvent is evaporated off and the oil obtained is taken up in 5 ml of acetone. 20 ml of ether is added and agitation is carried out until precipitation occurs. After filtration on frit and washing with ether, the desired product is obtained in the form of a beige powder (0.32 g, 56%).

Melting point: 180–189° C.

Example 6

5-(2-chlorophenyl)-1,2,3,6,7,9-hexahydro-3-hydroxy-N-(4-methoxy-2-nitrophenyl)-2-oxo-1-(2-phenylethyl)-8H-pyrido[4',3':4,5]thieno[2,3-e]-1,4-diazepine-8-carbothioamide 5-(2-chlorophenyl)-1,2,3,6,7,9-hexahydro-3-hydroxy-1-(2-phenylethyl)-8H-pyrido[4',3':4,5]thieno[2,3-e]-1,4-diazepine-2-one (0.167 g, 0.29 mmol) is dissolved in dichloromethane (2 ml). Triethylamine (0.06 ml, 0.44 mmol) then 4-methoxy 2-nitrophenylisothiocyanate (0.062 g, 0.29 mmol) are added. After agitation at 23° C. for 2 hours, the solvent is evaporated off. After purification by chromatography on a silica column (eluent: dichloromehane-methanol: 98-2), the fractions contining only the product are evaporated. The solid is taken up in ether and a drop of dichloromethame and a drop of acetone are added. After filtration on flit and washing the solid with ether, the desired product is obtained in the form of a yellow powder (0.08 g, 41%).

Melting point: 143–145° C.

Example 7

3-(7-amino-1-oxo-heptyloxy)-5-(2-chlorophenyl)-1,2,3,6,7,9-hexahydro-2-oxo-1-(2-phenylethyl)-8H-pyrido[4',3':4,5]thieno[2,3-e]-1,4-diazepine 1$^{st}$ Stage t-butyl 5-(2-chlorophenyl)$_3$-[7-[(1,1-methylethoxycarbonyl)amino]-1-oxo-heptyloxy]-1,2,3,6,7,9-hexahydro-2-oxo-1-(2-phenylethyl)-8H-pyrido[4',3':4,5]thieno[2,3-e]-1,4-diazepine-8-carboxylate 1 g of t-butyl 5-(2-chlorophenyl)-1,2,3,6,7,9-hexahydro-3-hydroxy-2-oxo-1-(2-phenylethyl)-8H-pyrido[4',3':4,5]thieno[2,3-e]-1,4-diazepine-8-carboxylate (1.8 mmol) is added to a mixture containing 7-[(1,1-methylethoxy)carbonyl]amino-heptanoic acid (0.45 g, 1.8 mmol), 1-(3-dimethylaminopropyl)-3-ethylcarbodiimide hydrochloride (0.42 g, 2.16 mmol), triethylamine (0.25 ml, 2.2 mmol) and 4-dimethylaminopyridine (0.22 g, 1.8 mmol) in dichloromethane (10 ml). Agitation is carried out for 24 hours at 23° C. then dichloromethane (30 ml) and ice-cooled water (20 ml) are added. Agitation is carried out and the reaction medium is left to decant. The organic phase is washed with water (2×20 ml) and dried over magnesium sulphate. After evaporation of the solvent with a rotary evaporator, chromatography is carried out on a silica column (eluent: ethyl acetate-heptane: 2-98 to 5-95). The fractions containing only the product are evaporated. The desired product is obtained in the form of a white amorphous powder (1.0 g, 71%).

Melting point 90–94° C.

NMR $^1$H (400 MHz, CDCl$_3$, δ); 1.24–1.62 (m, 27H); 1.95 (d, 1H); 2.5 (m, 2H); 2.8–2.9 (m, 4H); 3 (m, 1H); 3.82 (m, 1H); 3.86 (m, 1H); 4.35 (m, 2H); 4.70 (d, 1H) 5.94 (s, 1H); 6.73 (m, 1H); 7.2–7.3 (m, 5H); 7.47–7.56 (m, 4H).

IR (cm$^{-1}$): 3381; 2932; 1744 (v C=O ester); 1704–1677 (v C=O carbamates and v C=O lactame); 1165.

HPLC MS: 99.1% at 250 nm (MH+ found 779.3; MH+ theoretical 779.32).

2$^{nd}$ Stage 3-7-amino-1-oxo-heptyloxy)-5-(2-chlorophenyl)-1,2,3,6,7,9-hexahydro-1-(2-phenylethyl)-8H-pyrido[4',3':4,5]thieno[2,3-e]-1,4-diazepine-2-one The compound obtained in the previous stage (0.95 g, 1.2 mmol) is solubilieed in dichloromethane (2 ml). Trifluoroacetic acid (1 ml) is added and agitation is carried out for 16 hours at 23° C. After evaporation of the solvent with a rotary evaporator with the help of toluene (2×20 ml), purification by chromatography is carried out on a silica column (eluent: dichloromethane-methanol-triethylarmine: 94-6-0 to 89-10-1). After evaporation of the fractions containing only the product, the desired product is obtained in the form of a white powder (0.13 g, 19%).

NMR $^1$H (400 MHz, CDCl$_3$, δ): 1,28–1.64 (m, 13H); 2–2.2 (m, 1H); 2.52 (m, 2H); 2.73–2.87 (m, 4H); 3,2–3.4 (m, 1H); 3.82 (m, 1H); 4.26–4.37 (m, 2H); 5.94 (s, 1H); 7.22–7.55 (m, 9H); 7.95 (se, 2H).

HPLC MS: 96.5% at 250 nm (MH+ found 579.2; MH+ theoretical 579.22).

Example 8

3-(7-amino-1-oxo-heptyloxy)-5-(2-chlorophenyl)-1,2,3,6,7,9-hexahydro-N-(4-methoxy-2-nitrophenyl)-2-oxo-1-(2-phenylethyl)-8H-pyrido[4',3':4,5]thieno[2,3-e]-1,4-diazepine-8-carbothioamide 3-(7-amino-1-oxo-heptyloxy)-5-(2-chlorophenyl)-1,2,3,6,7,9-hexahydro-1-(2-phenylethyl)-8H-pyrido[4',3':4,5]thieno[2,3-c]-1,4-diazepine-2-one (0.11 g, 0.2 mmol) is solubilized in dichloromethane (2 ml). 4-methoxy-2-nitrophenylisothiocyanate (0.047 g, 0.22 mmol) is added. Agitation is carried out for 24 hours at 23° C. then isopropyl ether (20 ml) is added until precipitation of the solid. The heterogeneous mixture is agitated while adding ether (2 ml) and dichloromethane (0.5 ml). After filtration on frit and washing with isopropyl ether, the desired product is obtained in the form of an orange powder (0.045 g, 29%).

Melting point 90–95° C.

HPLC MS: 89.3% at 250 nm (MH+ found 789.2; MH+ theoretical 789.23).

Example 9
4-(7-amino-1-oxo-heptyl)-5-(2-chlorophenyl)-1,2,3,4,5,6,7,9-octahydro-1-(2-phenylethyl)-8H-pyrido[4',3':4,5]thieno[2,3-e]-1,4-diazepine-2-one $1^{st}$ Stage t-butyl 5-2-chlorophenyl)-1,2,3,4,5,6,7,9-octahydro-2-oxo-1-(2-phenylethyl)-8H-pyrido[4',3':4,5]thieno[2,3-e]-1,4-diazepine-8-carboxylate Acetic acid (12 ml) is added at ambient temperature and under argon to 4 g of t-butyl 5-(2-chlorophenyl)-1,2,3,6,7,9-hexahydro-2-oxo-1-(2-phenylethyl)-8H-pyrido[4',3':4,5]thieno[2,3-e]-1,4-diazepine-8-carboxylate (7.9 mmol). Then ethanol (60 ml) is added then the reaction medium is cooled down to 0° C. and sodium cyanoborohydride (1.5 g 2.4 mmol) is added slowly. The reaction mixture is agitated for one hour at 23° C. then poured into water then extraction is carried out with dichloromethane (2×100 ml). The organic phase is washed with a 10%/o solution of ammonium hydroxide (2×50 ml) and dried over magnesium sulphate. After filtration and evaporation of the solvent, the desired product is obtained in the form of an amorphous white solid (2.96 g, 75%).

NMR $^1$H (400 MHz, CDCl$_3$, δ); 1.36 (s, 9H); 1.65 (m, 1H); 2.16 (m, 1H); 2.78 (m, 1H); 2.91 (m, 1H); 3.38 (m, 1H); 3.42 (m, 2H); 3.50 (m, 2H); 4.20 (m, 1H); 4.40 (m, 1H); 4.50 (m, 1H); 5.46 (m, 1H); 7.30 (m, 8H); 7.43 (m, 1H).

IR (cm$^{-1}$): 3350 (v NH diazepine); 2950; 1687 (v C=O carbamate); 1672 (v C=O lactame); 1365; 1172; 751.

HPLC (UV): 99.4%

$2^{nd}$ Stage t-butyl 5-(2-chlorophenyl)-4-[7-[(1,1-methylethoxycarbonyl)amino]-1-oxo-heptyl]-1,2,3,4,5,6,7,9-octahydro-2-oxo-1-(2-phenylethyl)-8H-pyrido[4',3':4,5]thieno[2,3-e]-1,4-diazepine-8-carboxylate The product obtained during the previous stage (1 g, 1.86 mmol) is solubilized in 1,2-dichloroethane (20 ml). N-cyclohexyl carbodiimide resin, N'-methyl polystyrene Hl (2.3 g, 5.6 mmol) and tetrahydrofuran (0.5 ml) are added. 7-[(1,1-dimethylethoxy)carbonyl]amino-heptanoic acid (0.91 g, 3.7 mmol) is added and agitation is carried out for 48 hours at 23° C. The resin is filtered. The solvent is evaporated off and the reaction medium is taken up in dichloromethane (30 ml). Basic ion exchange resin is added, then agitation is carried out for 1 hour followed by filtering. After evaporation of the solvent with a rotary evaporator, the desired product is obtained in the form of an amorphous white solid (1.2 g, 86%).

NMR $^1$H (400 MHz, CDCl$_3$, δ): 1.15 (m); 1.25 (m); 1.36 (s); 1.41 (s); 1.52 (m); 2.85 (m); 2.16 (m); 2.22–2.40 (m); 2.58 (m); 2.81 (m); 3.48 (m); 3.75 (m); 3.90 (m); 4.35 (m); 4.40–4.60 (m); 6.0–7.0 (m); 7.30 (m); 7.18–7.40 (m).

IR (cm$^{-1}$): 3378 (v NH carbamate); 2974; 2930; 1700 (v C=O carbamates); 1676 (v C=O lactame); 1391; 1168; 759.

$3^{rd}$ Stage 4-(7-amino-1-oxo-heptyl)-5-(2-chlorophenyl)-1,2,3,4,5,6,7,9-octahydro-1-(2-phenylethyl)-8H-pyrido[4',3':4,5]thieno[2,3-e]-1,4-diazepine-2-one A solution containing the compound obtained during the previous stage (1 g, 1.3 mmol) and trifluoroacetic acid (3 ml) in 10 ml of dichloromethane is agitated for 4 hours at 23° C. The reaction mixture is evaporated while taking up in toluene (2×30 ml) and ether (2×30 ml). The residue is agitated in a mixture of solvent containing ether-acetone-dichloromethane (90-0.5-0.5) for 5 minutes, followed by filtering on frit then washing with ether. The desired product is obtained in the form of a white powder (1.0 g, 96%).

Melting point: 149–152° C.

NMR $^1$H (400 MHz, CDCl$_3$, δ): 1.20–1.57 (m); 1.86–2.25 (m); 2.56–2.79 (m); 2.91 (m); 3.30 (m); 3.79–3.91 (m); 4.27–4.37 (m); 6.07–6.63 (m); 6.63–6.99 (m); 7.01–7.76 (m); 9.45 (m).

Example 10
4-(7-amino-1-oxo-heptyl)-5-(2-chlorophenyl)-1,2,3,4,5,6,7,9-octahydro-N-(4-methoxy-2-nitrophenyl)-2-oxo-1-(2-phenylethyl)-8H-pyrido[4',3':4,5]thieno[2,3-e]-1,4-diazepine-8-carbothioamide Triethylamine (0.22 ml, 1.5 mmol) is added to 0.5 g of 4-7-amino-1-oxo-heptyl)-5-2-chlorophenyl)-1,2,3,4,5,6,7,9-octahydro-1-(2-phenylethyl)-8H-pyrido[4',3':4,5]thieno[2,3-e]-1,4-diazepine-2-one (0.63 mmol) dissolved in dichloromethane (12 ml). Then 4-methoxy-2-nitrophenylisothiocyanate (0.146 g, 0.69 mmol) is added and agitation is carried out for one hour at 23° C. then the solvent is evaporated off with a rotary evaporator. After purification by chromatography on a silica column (eluent: dichloromethane-methanol-ammonium hydroxide: 98-2-0 to 95-5-0.5), the fractions containing only the product are evaporated then a minimum amount of dichloromethane then a solution of 1M hydrochloric acid (0.2 ml) are added. Agitation is carried out for 30 minutes at 23° C. then the product obtained is filtered on frit. After washing with ether, the desired product is obtained in the form of an orange powder (0.12 g, 25%).

Melting point: from 160° C.

NMR $^1$H (400 MHz, CDCl$_3$, δ): 1.32 (m); 1.57 (m); 1.9 (m); 2.10 (m); 2.33 (m); 2.43–2.75 (m); 3.57–3.35 (m); 3.83 (m); 4.35 (m); 5.00 (m); 5.30 (m); 6.65 (m); 7.00 (m); 7.50–7.01 (m); 7.89 (m); 9.69 (m).

IR (cm$^{-1}$): 3420 (v NH); 2930; 1670; 1664; 1655; 1649; 1532; 1348.

HPLC (UV): 96%

Example 11
5-2-chlorophenyl)-1,2,3,4,5,6,7,9-octahydro-4-(3-methyl-2-butenyl)-2-oxo-1-(2-phenyl-ethyl)-8H-pyrido[4',3':4,5]thieno[2,3-e]-1,4-diazepine $1^{st}$ Stage t-butyl 5-(2-chlorophenyl)-1,2,3,4,5,6,7,9-octahydro-4-(3-methyl-2-butenyl)-2-oxo-1-(2-phenyl-ethyl)-8H-pyrido[4',3':4,5]thieno[2,3-e]-1,4-diazepine-8-carboxylate 0.5 g of t-butyl 5-2-chlorophenyl)-1,2,3,4,5,6,7,9-octahydro-2-oxo-1-(2-phenylethyl)-8H-pyrido[4',3':4,5]thieno[2,3-e]-1,4-diazepine-8-carboxylate (1 mmol) is dissolved in anhydrous tetrahydrofuiran (20 ml). Sodium hydride dispersed at 60% (0.028 g, 1.1 mmol) is added by portions. The reaction meum is left until release ends then 1-bromo-3-methyl-2-butene (0.125 ml, 1.1 lmmol) is added dropwise. Agitation is carried out for 3 hours at 23° C. and the reaction medium is heated all night at 60° C. then the halogenated derivative (0.125 ml, 1.1 mmol) is added. After heating for 48 hours at 60° C., the reaction medium is poured into a saturated solution of ammonium chloride (30 ml) then ethyl acetate (30 ml) is added. After decanting, the aqueous phase is extracted with ethyl acetate (30ml). The organic phase is dried over magnesium sulphate, filtered and the solvent-is evaporated off. After purification by chromatography on a silica column (eluent: ethyl acetate-heptane: 20-80 to 50-50), the fractions containing only the product are evaporated and the desired product is obtained in the form of a pale yellow amorphous powder (0.47 g, 79%).

NMR $^1$H (400 MHz, CDCl$_3$, δ); 1.37 (s, 9H); 1.53 (s, 3H); 1.67 (s, 3H); 2.06–2.48 (m, 2H); 2.49 (m, 1H); 2.61 (m, 1H); 3.11 (m, 2H); 3.23 (m, 1H); 3.3 (m, 1H); 3.48 (m, 2H); 3.70 (m, 1H); 4.46 (m, 1H); 4.46 (m, 2H); 5.17 (m, 2H); 5.17 (m, 2M); 7.17–7.55 (m, 9H).

IR (cm$^{-1}$): 2974; 2926; 2855; 1697 (v C=O carbamate); 1676 (v C=O Lactae); 1365; 1165; 750; 699.

HPLC (UV): 98.5%

2nd Stage 5-(2-chlorophenyl)-1,2,3,4,5,6,7,9-octahydro-4-(3-methyl-2-butenyl)-1-(2-phenylethyl)-8H-pyrido[4',3':4,5]thieno[2,3-e]-1,4-diazepine-2-one The compound obtained during the previous stage (0.4 g, 0.65 mmol) is dissolved in dichloromethane (5 ml) then trifluoroacetic acid (2 ml) is added. Agitation is maintained for 2 hours at 23° C. then the solvent and the excess acid are evaporated off with a rotary evaporator. After purification by chromatography on a silica column (eluent: dichloromethane-methanol-ammonium hydroxide: 98-0-0 to 98-2-0.2), the fractions containing only the product are evaporated. The residual oil is taken up in ether (20 ml). After cooling down, 1M hydrochloric ether (0.2 ml) is added and agitation is carried out for 15 minutes and the solid obtained is then filtered on Srit and washed with ether. The desired product is obtained in the form of a pale yellow powder (0.11 g, 33%).

Melting point: 114–118° C.

NMR $^1$H (400 MHz, CDCl$_3$, δ): 1.55 (s, 3H); 1.69 (s, 3H); 2.3–2.65 (m, 4H); 3.14–3.40 (m, 7H); 3.68 (m, 1H); 3.97 (m, 1H); 4.27 (m, 2H); 5.14 (m, 2H); 7.16–7.56 (m, 9H); 9.50 (m, 2H).

Example 12

5-(2-chlorophenyl)-1,2,3,4,5,6,7,9-octahydro-4-(3-methyl-2-butenyl)-N-(4-methoxy-2-nitrophenyl)-2-oxo-1-(2-phenylethyl)-8H-pyrido[4',3':4,5]thieno[2,3-e]-1,4-diazepine-8-carbothioamide 0.22 g of 5-2-chlorophenyl)-1,2,3,4,5,6,7,9-octahydro4-(3-methyl-2-butenyl)-1-(2-phenylethyl)-8H-pyrido[4',3':4,5]thieno[2,3-e]-1,4-diazepine-2-one (0.43 mmol) is solubilized in dichloromethane (2 ml) then 4-methoxy-2-nitrophenylisothiocyanate (0.1 g, 0.48 mmol) is added. After agitation for 1 hour at 23° C., the solvent is evaporated off. After purification by chromatography on a silica column (eluent: dichloromethane-methanol: 100-0 to 99.5-0.5), the fractions containing only the product are evaporated and the solid obtained is taken up in isopentane (20 ml). Ether (2 ml) is added then agitation is carried out for 20 minutes, followed by filtering on fiit, washing with a minimum amount of isopropyl ether and isopentane. The desired product is obtained in the form of a pale yellow powder (0.19 g, 61%).

Melting point: 80–84° C.

NMR $^1$H (400 MHz, CDCl$_3$, δ): 1.55 (s, 3H); 1.69 (s, 3H); 2.25–2.67 (m, 3H); 3.07–3.26 (m, 4H); 3.70 (m, 1H); 3.84 (s, 3H); 3.96 (m, 2H); 4.10 (m, 1H); 5.00–5.18 (m, 4H); 6.86–7.59 (m, 13H); 9.52 (s, 1H).

IR (cm$^{-1}$): 3482; 2974; 2926; 2855; 1671 (ν C=O lactame); 1500; 1302.

HPLC (UV): 98%

Example 13

5-(2-chlorophenyl)-1,3,4,5,6,7,8,9-octahydro-1-(2-phenylethyl)-2H-pyrido[4',3':4,5]thieno[2,3-e]-1,4-diazepine-2-one t-butyl 5-(2-chlorophenyl)-1,2,3,4,5,6,7,9-octahydro-2-oxo-1-(2-phenylethyl)-8H-pyrido[4',3':4,5]thieno[2,3-e]-1,4-diazepinme-8-carboxylate (0.5 g, 0.93 mmol) is solubilized in anhydrous dichloromethane (10 ml). Trifluoroacetic acid (3 ml) is added and agitation is carried out at a temperature around 20° C. for two hours. The solvents are evaporated taking up several times with totuene. A mixture of solvents (ether-dichloromethane-acetone 30-0.5-0.5 ml) is added then the reaction mixture is agitated for two hours until precipitation occurs. After filtration on frit, washing with ether then drying under vacuum, the desired product is obtained in the form of a yellow powder (0.34 g, 85%)

Melting point: 128–130° C.

HPLC MS: 97% to 270 nm (MH+ found 438.1; MH+ theoretical 438.14).

Example 14

5-(2-chlorophenyl)-1,2,3,4,5,6,7,9-octahydro-N-(4-methoxy-2-nitro-phenyl)-2-oxo-1-(2-pentyl)-8H-pyrido[4',3':4,5]thieno[2,3-e]-1,4-diazepine-8-carbothioamide Acetic acid (0.5 ml) is added to 0.16 g of 5-(2-chiorophenyl)-1,2,3,6,7,9-hexahydro-N-(4-methoxy-2-nitrophenyl)-2-oxo-1-(2-pentyl)-8H-pyrido[4',3':4,5]thieno[2,3-e]-1,4-diazepine-8-carbothioamide (0.26 mmol). Ethanol (3.5 ml) is added to this yellow suspension then acetic acid (1 ml) and finally sodium cyanoborohydride (0.033g, 0.52 mmol) are added dropwise. The reaction mixture is agitated for one hour then it is heated for one hour at 40° C. until solubilization. Then agitation is carried out for 2 hours at 22° C. The reaction medium is poured into ice-cooled water (30 ml), followed by agitation, filtering then washing abundantly with water. After drying under vacuum without heating, the desired product is obtained in the form of an orange powder (0.145 g, 83%)

Melting point: from 90° C.

HPLC MS: 94% at 240 nm (M found 614.1; MH+ theoretical 614.17).

Other compounds, obtained according to similar to those described in Examples 1 to 14, are presented below. Examples 15 to 45 illustrate the compounds in which A—B represents —C=N—; Examples 46 to 70 illustrate the compounds in which A—B represents —C—N(R$_5$)—.

The R$_1$; R'$_1$; Y; R$_2$; R$_{3a}$; R$_{3b}$; X; n; R'$_4$; R"4 radicals as well as the melting point (in ° C. optionally completed by the state of the compound (gb: free base; st: salt (TFA); sh: salt (HCl); * amorphous state) of the examples 15 to 45 have respectively the following meanings:

Ex 15: H;-;-; 2-Cl-Phe; H; H; O; 2; H; Phe; 84-88 (*fb);

Ex 16: H;-;-; 2-Cl-Phe; H; H; O; 0; H; phenylcarbonyl; 132–134 (fb);

Ex 17: H;-;-; 2-Cl-Phe; H; H; O; 0; H; Phe; 135–136 (fb);

Ex 18: H;-;-; 2-Cl-Phe; H; H; O; 0; H; cyclohexyl; 189–190 (fb);

Ex 19: H;-;-; 2-Cl-Phe; H; H; O; 4; H; H; 144–150 (fb);

Ex 20: H;-;-; 2-Cl-Phe; H; H; O; 2; Phe; Phe; 104–108 (fb);

Ex 21: H;-;-; 2-Cl-Phe; H; H; O; 2; Me; Me; 74–77 (*fb);

Ex 22: H;-;-; 2-Cl-Phe; H; H; O; 0; H; adamantyl; 222–230 (sh);

Ex 23: H;-;-; 2-Cl-Phe; H; H; O; 1; H; pyridyl; 82 (*fb);

Ex 24: H;-;-; Phe; H; H; O; 1; H; Phe; >80 (*fb);

Ex 25: H;-;-; 4-Cl-Phe; H; H; O; 1; H; Phe; 118–120 (fb);

Ex 26: H;-;-; 2-F-Phe; H; H; O; 1; H; Phe; >85 (*fb);

Ex 27: H;-;-; 4-F-Phe; H; H; Q; 1; H; Phe; >70 (*fb)

Ex 28: H;-;-; 2-Me-Phe; H; H; O; 1; H; Phe; 8082 (*fb);

Ex 29: H;-;-; t-butyl; H; H; O; 1; H; Phe; 160–162 (sh);

Ex 30: R'$_1$—NH—C(Y)—; 2-NO$_2$-4-MeO-Phe; S; 2-Cl-Phe; H; H; O; 2; H; Phe; 141–143;

Ex 31: R'$_1$—NH—C(Y)—; 2-NO$_2$-4-MeO-Phe; S; 2-Cl-Phe; H; H; O; 0; H; phenylcarbonyl; 182–184;

Ex 32: R'$_1$—NH—C(Y)—; 2-NO$_2$-4-MeO-Phe; S; 2-Cl-Phe; H; H; O; 0; H; Phe; 190–192;

Ex 33: R'$_1$—NH—C(Y)—; 2-NO$_2$-4-MeO-Phe; S; 2-Cl-Phe; H; H; O; 4; H; H; 158–160;

Ex 34: R'$_1$—NH—C(Y)—; 2-NO$_2$-4-MeO-Pne; S; 2-Cl-Phe; H; H; O; 0; H; cyclohexyl; 183–184;

Ex 35: R'$_1$—NH—C(Y)—; 2-NO$_2$-4-MeO-Phe; S; 2-Cl-Phe; H; H; O; 2; Phe; Phe; 156158;

Ex 36: R'$_1$—NH—C(Y)—; 2-NO$_2$-4-MeO-Phe; S; 2-Cl-Phe; H; H; O; 2; Me; Mc; 149–154;

Ex 37: R'$_1$—NH—C(Y)—; 2-NO$_2$-4-MeO-Phe; S; 2-Cl-Phe; H; H; O; 0; H; adamantyl; 210–214;

Ex 38: R'₁—NH—C(Y)—; 2-NO₂-4-MeO-Phe; S; 2-Cl-Phe; H; H; O; 1; H; pyridyl; 131;
Ex 39: R'₁—NH—C(Y)—; 2-NO₂-4-MeO-Phe; S; Phe; H; H; O; 1; H; Phe; 148–150;
Ex 40: R'₁—NH—C(Y)—; 2-NO₂-4-MeO-Phe; S; 4-Cl-Phe; H; H; O; 1; H; Phe; >130 (*)
Ex 41: R'₁—NH—C(Y)—; 2-NO₂-4-MeO-Phe; S; 2-F-Phe; H; H; O; 1; H; Phe; >122 (*);
Ex 42: R'₁—NH—C(Y)—; 2-NO₂-4-MeO-Phe; S; 4-F-Phe; H; H; O; 1; H; Phe; 108–110;
Ex 43: R'₁—NH—C(Y)—; 2-F₃C-Phe; O; 4-F-Phe; H; H; O; 1; H; Phe; >85 (*);
Ex 44: R'₁—NH—C(Y)—; 2-NO₂-4-MeO-Phe; S; 2-Me-Phe; H; H; O; 1; H; Phe; 120–130;
Ex 45: R'₁—NH—C(Y)—; 2-NO₂-4-MeO-Phe; S; t-butyl; H; H; O; 1; H; Phe; 177;

The $R_1$; $R'_1$; Y; $R_2$; $R_{3a}$; $R_{3b}$; X; n; $R'_4$; $R''_4$ and $R_5$ radicals as well as the melting point (in ° C. optionally completed by the state of the compound (fb: free base; st: salt (TFA); sh: salt (HCl); *amorphous state) of the examples 46 to 70 have respectively the following meanings:

Ex 46: H;-;-; 2-Cl-Phe; H; H; H; O; 2; Me; Me; 128–132 (sh);
Ex 47: H;-;-; 2-Cl-Phe; H; H; aminopentylcarbonyl; O; 1; H; Phe; 200–202 (st);
Ex 48: H;-;-; 2-Cl-Phe; H; H; indolylmethylcarbonyl; O; 1; H; Phe; 160 (st);
Ex 49: H;-;-; 2-Cl-Phe; H; H; amfinobutylcarbonyl; O; 1; H; Phe; 120124 (st);
Ex 50: H;-;-; 2-Cl-Phe; H; H; propylcarbonyl; O; 1; H; Phe; 214 (st);
Ex 51: H;-;-; 2-Cl-Phe; H; H; cyclopentyl-methylcarbonyl; O; 1; H; Phe; 175–185 (st);
Ex 52: H;-;-; 2-Cl-Phe; H; H; phenyl; O; 1; H; Phe; >155 (st);
Ex 53: H;-;-; 2-Cl-Phe; H; H; phenylethylcarbonyl; O; 1; H; Phe; 149–151 (st);
Ex 54: H;-;-; 2-Cl-Phe; H; H; 4-(L-alanoyloxymthyl)benzyl carbonyl; O; 1; H; Phe; >140 (st).
Ex 55: H;-;-; 2-Cl-Phe; H; H; 4-(aminomethyl)phenyl carbonyl; O; 1; E; Phe (fb).
Ex 56: H;-;-; Phe; H; H; NH₂—CH₂—C(O) NH—CH₂—C(O)—NH—C(O)—; O; 2; Me; Me; 122–128 (st).
Ex 57: H;-;-; neopentyl; H; H; aminohexylcarbonyl; O; 1; H; Phe; <50.
Ex 58: H;-;-; isobutyl; H; H; aminohexylcarbonyl; O; 1; H; Phe; from 60° C. (*)
Ex 59: H;-;-; isobutyl; H; H; H; O; 1; H; Phe; 202–206 (sh).
Ex 60 R'₁—NH—C(Y)—; 2-NO₂-4-MeO-Phe; S; 2-Cl-Phe; H; H; propylcarbonyl; O; 1; H; Phe; 163–165
Ex 61: R'₁—NH—C(Y)—; 2-NO₂-4-MeO-Phe; S; 2-Cl-Phe; H; H; cyclopentyl-methylcarbonyl; O; 1; H; Phe; 177–178;
Ex 62: R'₁—NH—C(Y)—; 2-NO₂-4-MeO-Phe; S; 2-Cl-Phe; H; H; phenyl-propylcarbonyl; O; 1; H; Phe; 202–203;
Ex 63: R'₁—NH—C(Y)—; 2-NO₂-4-MeO-Phe; S; 2-Cl-Phe; H; H; phenylethylcarbonyl; O; 1; H; Phe; 114–115;
Ex 64: R'₁—NH—C(Y)—; 2-NO₂-4-MeO-Phe; S; 2-Cl-Phe; H; H; aminobutylcarbonyl; O; 1; H; Phe; 166–172 (sh);
Ex 65: R'₁—NH—C(Y)—; 2-NO₂-4-MeO-Phe; S; 2-1-Phe; H; H; indolylmethylcarbonyl; O; 1; H; Phe; 193–196;
Ex 66: R'₁—NH—C(Y)—; 2-NO₂-4-MeO-Phe; S; 2-Cl-Phe; H; H; aminopentylcarbonyl; O; 1; H; Phe; >150 (sh).
Ex 67: R'₁—NH—C(Y)—; 2-NO₂-4-MeO-Phe; S; Phe; H; H; NH₂—CH₂—C(O)—NH—CH₂—C(O)—NH—C(O)—; O; 2; Me; Me; 184–188 (sh).
Ex 68: R'₁—NH—C(Y)—; 2-NO₂-4-MeO-Phe; S; Phe; H; H; aminohexylcarbonyl; O; 2; Me; Me; 160–166 (sh).
Ex 69: R'₁—NH—C(Y)—; 2-NO₂-4-MeO-Phe; S; neopentyl; H; H; aminohexylcarbonyl; O; 1; H; Phe; 116–118 (bl).
Ex 70: R'₁—NH—C(Y)—; 2-NO₂-4-MeO-Phe; S; isobutyl; H; H; aminohexylcarbonyl; O; 1; H; Phe; from 110° C. (bl).

Pharmacological Study

Study of the bond to somatostatin receptors.

The affinity of the compounds of the invention on human somatostatin receptors is determined by measurement of the inhibition of the bond of somatostatin-14 labelled with iodine-125 ([125I-Tyr11]SRIF-14) on the relceptors of transfected CHO-K11-cells.

The human genes coding for each of the subtypes of somatostatin receptors, sst1, sst2, sst3, sst4 and sst5, have been isolated and subcloned (*Proc. Natl. Acad Sci.* USA 1992, 89, 251–255; *J. Biol. Chem.* 1992, 267, 20422–20428; *Mol. Pharmacol.* 1992, 42, 2136–2142; *Proc. Natl. Acad. Sci.* USA 1993, 90, 4196–4200; *Mol. Pharmacol.* 1994, 46, 291–298). The expression vectors were constructed and the cloned cell lines were obtained by transfection in mammalian CHO-K1-cells. The plasmid pRSVY-neo was included as a selection factor.

The CHO-K1 cells which express in a stable fashion the human somatostatin receptors are cultured in an RPMI 1640 medium containing 10% of foetal calf serum and 0.4 mg/ml of geneticin. The cells are collected with EDTA at 0.5 mM and centrifuged at 500 g for 5 minutes at 4° C. The pellet is resuspended in Tris 50 mM, pH 7.4 and centrifuged twice at 500 g for 5 minutes at 14° C. The cells are lysed by sonication then centrifuged at 39000 g for 10 minutes at 4° C. The pellet is resuspended in the same buffer and centrifuged at 50000 g for 5 minutes at 4° C. The cell membranes obtained are stored at −80° C. until the day of the experiments.

The competitive inhibition experiments of the bond of [125I-Tyr11]SRIF-14 are carried out in duplicate in 96-well plates. The cell membranes at 10 (sst2 and ss5) or 20 (sst1, sst3 and sst4) µg of proteins/well, were incubated with [125I-Tyr11]SRIF-14 at 0.05 nM (sst2) or 0.1 nM (sst1, sst3, sst4 or sst5) for 500 (sst3), 60 (sst1 and sst2 70 (sst5) or 90 (sst4) minutes at 37° C. in a HEPES 50 mM, pH 7.4, BSA 0.2%, MgCl₂ 5 mM, Trasylol 200 KIU/ml, bacitricin 0.02 mg/ml, phenylmethylsulphonyl fluoride 0.02 mg/ml buffer.

After the incubation period, [125I-Tyr11]SRIF-14 free or bound to the somatostatin receptors is separated on a filtration unit (Filtermate 196, Packard) with Unifilter GF/C (Packard) filter plates pretreated with 0.1% polyethylenimine. After washing with HEPES 50 mM, the radioactivity present on the filters is measured using a Top Count (Packard) counter.

The specific bond obtained by subtracting die non-specific bond (determined in the presence of 0.1 µM of somatostatin-14) from the total bond. The results are analyzed by non-linear regression (MDL) and the inhibition constants (Ki) determined are comprised between 10 and 10000 nM.

What is claimed is:

1. A compound of the formula

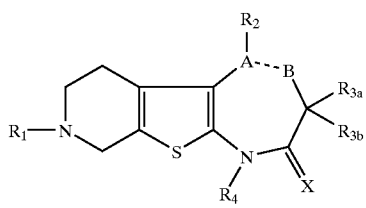

in racemic, or enantiomeric or diastereoisomeric form or mixtures thereof, wherein $R_1$ is hydrogen or $R'_1$—NH—C(Y)—;

$R'_1$ is unsubstituted or substituted aryl or heteroaryl;

$R_2$ is selected from the group consisting of alkyl of 1 to 6 carbon atoms, trifluoromethyl and phenyl unsubstituted or substituted with at least one member of the group consisting of hydroxy, halo, lower alkyl anrd lower alkoxy of 1 to 6 carbon atoms, X and Y are independently O or S;

$R_{3a}$ is selected from the group consisting of hydrogen, alkyl of 1 to 6 carbon atoms, hydroxy and —OC(O)$R'_{3a}$;

$R'_{3a}$ is alkyl of 1 to 10 carbon atoms unsubstituted or substituted with at least one member of the group consisting of: cycloalkyl; heterocycloalkyl; aryl; heteroaryl; guanidyl unsubstituted or substituted by nitro or cyano; or —NR″$_{3a}$R‴$_{3a}$; R″$_{3a}$ and R‴$_{3a}$ are individually selected from the group consisting of hydrogen, lower alkyl, aryl, lower arylalkyl, lower heteroarylalkyl, alkylcarbonyl and alkoxycarbonyl;

$R_{3b}$ is hydrogen or alkyl of 1 to 6 carbon atoms;

$R_4$ is —(CH$_2$)$_n$—CHR'$_4$R″$_4$;

n is an integer from 0 to 6;

R'$_4$ and R″$_4$ are individually selected from the group consisting of hydrogen, alkyl of 1 to 6 carbon atoms, cycloalkyl of 3 to 6 carbon atoms, lower cycloalkyl alkyl, aryl, lower aralkyl, heteroaryl, lower heteroarylalkyl, arylcarbonyl and adamantyl, all unsubstituted or substituted;

A—B is —C=N— or —C—N(R$_5$)—;

$R_5$ is selected from the group consisting of hydrogen, alkyl of 1 to 6 carbon atoms, alkenyl of up to 6 carbon atoms and —C(O)—(CH$_2$)$_p$—R'$_5$;

R'$_5$ is selected from the group consisting of hydrogen, amino, lower alkyl amino, di(lower alkyl)amino, cycloalkyl, heterocycloalkyl guanidyl unsubstituted or substituted by nitro or cyano, aryl optionally substituted, heteroaryl and —NH—C(O)—(CH$_2$)$_c$—NH—C(O)—(CH$_2$)$_d$—NH$_2$;

p is an integer from 0 to 10;

c and d are independently 0, 1, 2 or 3; and a non-toxic, pharmaceutically acceptable acid addition salt thereof.

2. A compound of claim 1 wherein the individual substituents on the aryl or heteroaryl of R'$_1$, are selected from the group consisting of lower alkyl, lower alkoxy, lower alkylthio, lower alkoxy carbonyl, lower alkyl sulfonyl, halo, trifluoromethyl, trifluoromethyloxy, hydroxy, nitro, cyano, aryl, aryloxy, cycloalkyl and heterocycloalkyl;

the substituents on the phenyl of $R_2$, are selected from the group consisting of hydroxy, halo, lower alkyl and lower alkoxy, the R'$_4$ and R″$_4$ substituents of alkyl, cyclalkyl, cycloalkyl alkyl, aryl, arylalkyl, heteroaryl, heteroarylalkyl, arylcarbonyl or adamantyl are individually selected from the group consisting of hydroxy, halo, trifluoromethyl, lower alkyl and lower alkoxy;

the R'$_5$ substituents of aryl are individually selected from the group consisting of alkyl or alkoxyalkyl, both unsubstituted or substituted by oxy or amino.

3. A compound of claim 1 wherein

R'$_1$ is aryl unsubstituted or substituted by at least one member of the group consisting of lower alkoxy, trifluoromethyl and nitro;

$R_2$ is alkyl of 1 to 6 carbon atoms or phenyl unsubstituted or substituted by at least one member of the group consisting of halo and alkyl of 1 to 6 carbon atoms;

$R_{3a}$ is selected from the group consisting of hydrogen, hydroxy and —OC(O)R'$_{3a}$;

R'$_{3a}$ is alkyl containing 1 to 6 carbon atoms unsubstituted or substituted by at least one —NR″$_{3a}$R‴$_{3a}$ in which R″$_{3a}$ and R‴$_{3a}$ are individually hydrogen, or alkyl of 1 to 6 carbon atoms or alkoxycarbonyl of 2 to 7 carbon atoms;

$R_{3b}$ is hydrogen;

R'$_4$ and R″$_4$ are individually selected from the group consisting of hydrogen, alkyl of 1 to 6 carbon atoms, cycloalkyl of 3 to 6 carbon atoms, aryl heteroaryl, arylcarbonyl and adamantyl and;

A— is —C=N—.

4. A compound of claim 3 wherein

R'$_1$ is phenyl unsubstituted or substituted by at least one member of the group consisting of alkoxy of 1 to 6 carbon atoms, trifluoromethyl and nitro;

$R_2$ is alkyl of 1 to 6 carbon atoms or phenyl unsubstituted or substituted by at least one member of the group consisting of methyl, chloro and fluoro;

R'$_{3a}$ is alkyl of 1 to 6 carbon atoms unsubstituted or substituted by at least one amino;

R'$_4$ and R'$_4$ are independently selected from the group consisting of hydrogen, alkyl of 1 to 6 carbon atoms, cyclohexyl, phenyl, pyridyl, phenylcarbonyl and adamantyl.

5. A compound of claim 1 wherein A—B is —C=N— and $R_1$; R'$_1$; Y; $R_2$; $R_{3a}$; $R_{3b}$; X; n; R'$_4$; R″$_4$ respectively have the following meanings:

H;-;-; 2-Cl-Phe; H; H; O; 1; H, Phe;
H;-;-; 2-Cl-Phe; H; H; S; 1; H; Phe;
H;-;-; 2-Cl-Phe; H; H; O; 2; H; Phe;
H;-;-; 2-Cl-Phe; H; H; O; 0; H; phenylcarbonyl;
H;-;-; 2-Cl-Phe; H; H; O; 0; H; Phe;
H;-;-; 2-Cl-Phe; H; H; O; 0; H; cyclohexyl;
H;-;-; 2-Cl-Phe; H; H; O; 4; H; H;
H;-;-; 2-Cl-Phe; H; H; O; 2; Phe; Phe;
H;-;-; 2-Cl-Phe; H; H; O; 2; Me; Me;
H;-;-; 2-Cl-Phe; H; H; O; 0; H; adamantyl;
H;-;-; 2-Cl-Phe; H; H; O; 1; H; pyridyl;
H;-;-; Phe; H; H; O; 1; H; Phe;
H;-;-; 4-Cl-Phe; H; H; O; 1; H; Phe;
H;-;-; 2-F-Phe; H; H; O; 1; H; Phe;
H;-;-; 2-F-Phe; H; H; O; 1; H; Phe;
H;-;-; 2-Me-Phe; H; H; O; 1; H; Phe;
H;-;-; t-butyl; H; H; O; 1; H; Phe;
H;-;-; 2-Cl-Phe; OH; H; O; 1; H; Phe;

H;-;-; 2-Cl-Phe; OC(O)—(CH$_2$)$_6$NH$_2$; H; O; 1; H; Phe;
R'$_1$—NH—C(Y)—; 2-NO$_2$-4-MeO-Phe; S; 2-Cl-Phe; H; H; O; 1; H; Phe;
R'$_1$—NH—C(Y)—; 2-NO$_2$-4-MeO-Phe; S; 2-Cl-Phe; H; H; O; 2; H; Phe;
R'$_1$—NH—C(Y)—; 2-NO$_2$-4-MeO-Phe; S; 2-Cl-Phe; H; H; S; 1; H; Phe;
R'$_1$—NH—C(Y)—; 2-NO$_2$-4-MeO-Phe; S; 2-Cl-Phe; H; H; O; 0; H; phenylcarbonyl;
R'$_1$—NH—C(Y)—; 2-NO$_2$-4-MeO-Phe; S; 2-Cl-Phe; H; H; O; 0; H; Phe;
R'$_1$—NH—C(Y)—; 2-NO$_2$-4-MeO-Phe; S; 2-Cl-Phe; H; H; O; 4; H; H;
R'$_1$—NH—C(Y)—; 2-NO$_2$-4-MeO-Phe; S; 2-Cl-Phe; H; H; O; 0; H; cyclohexyl;
R'$_1$—NH—C(Y)—; 2-NO$_2$-4-MeO-Phe; S; 2-Cl-Phe; H; H; O; 2; Phe; Phe;
R'$_1$—NH—C(Y)—; 2-NO$_2$-4-MeO-Phe; S; 2-Cl-Phe; H; H; O; 2; Me; Me;
R'$_1$—NH—C(Y)—; 2-NO$_2$-4-MeO-Phe; S; 2-Cl-Phe; H; H; O; 0; H; adamantyl;
R'$_1$—NH—C(Y)—; 2-NO$_2$-4-MeO-Phe; S; 2-Cl-Phe; H; H; O; 1; H; pyridyl;
R'$_1$—NH—C(Y)—; 2-NO$_2$-4-MeO-Phe; S; Phe; H; H; O; 1; H; Phe;
R'$_1$—NH—C(Y)—; 2-NO$_2$-4-MeO-Phe; S; 4-Cl-Phe; H; H; O; 1; H; Phe;
R'$_1$—NH—C(Y)—; 2-NO$_2$-4-MeO-Phe; S; 2-F-Phe; H; H; O; 1; H; Phe;
R'$_1$—NH—C(Y)—; 2-NO$_2$-4-MeO-Phe; S; 4-F-Phe; H; H; O; 1; H; Phe;
R'$_1$—NH—C(Y)—; 2-F$_3$C-Phe; S; 4-F-Phe; H; H; O; 1; H; Phe;
R'$_1$—NH—C(Y)—; 2-NO$_2$-4-MeO-Phe; S; 2-Me-Phe; H; H; O; 1; H; Phe;
R'$_1$—NH—C(Y)—; 2-NO$_2$-4-MeO-Phe; S; t-butyl; H; H; O; 1; H; Phe;
R'$_1$—NH—C(Y)—; 2-NO$_2$-4-MeO-Phe; S; 2-Cl-Phe; OH; H; O; 1; H; Phe;
R'$_1$—NH—C(Y)—; 2-NO$_2$-4-MeO-Phe; S; 2-Cl-Phe; OC(O)—(CH$_2$)$_6$NH$_2$; H; O; 1; H; Phe.

6. A compound of claim 1 wherein
R'$_1$, is aryl unsubstituted or substituted by at least one member of the group consisting of alkoxy of 1 to 6 carbon atoms and nitro;
R$_2$ is alkyl of 1 to 6 carbon atoms or phenyl unsubstituted or substituted by at least one halo;
R$_{3a}$ and R$_{3b}$ are hydrogen;
R'$_4$ and R''$_4$ are individually selected from the group consisting of hydrogen, alkyl of 1 to 6 carbon atoms and aryl;
A—B is —C—N(R$_5$)—;
R$_5$ is selected from the group consisting of hydrogen, alkenyl of up to 6 carbon atoms and —C(O)—(CH$_2$)$_p$—R'$_5$; and R'$_5$ is selected from the group consisting of hydrogen, amino, lower alkyl amino, di(lower alkyl) amino, cycloalkyl, heterocycloalkyl, guanidyl unsubstituted or substituted by nitro or cyano, aryl optionally substituted, heteroaryl and —NH—C(O)—(CH$_2$)$_c$—NH—C(O)—(CH$_2$)$_d$—NH$_2$;
p is an integer from 0 to 10;
c and d are independently 0, 1, 2 or 3; and a non-toxic, pharmaceutically acceptable acid addition salt thereof.

7. A compound of claim 1 wherein
R'$_1$ is phenyl unsubstituted or substituted by at least one member of the group consisting of alkoxy of 1 to 6 carbon atoms and nitro;
R$_2$ is alkyl of 1 to 6 carbon atoms or phenyl unsubstituted or substituted by chloro;
R'$_4$ and R''$_4$ are individually selected from the group consisting of hydrogen, alkyl of 1 to 6 carbon atoms and phenyl;
R$_5$ is selected from the group consisting of hydrogen, pentenyl and —C(O)—R'$_5$;
R'$_5$ is selected from the group consisting of hydrogen, amino, cyclopentyl, indolyl, —NH—C(O)—CH$_2$—NH—C(O)—CH$_2$—NH$_2$, and phenyl unsubstituted or substituted by at least one member of the group consisting of alkyl and alkoxyalkyl of 1 to 6 carbon atoms unsubstituted or substituted by oxy or amino.

8. A compound of claim 1 wherein A—B is —C—N (R$_5$)— and R$_1$; R'$_1$; Y; R$_2$; R$_{3a}$; R$_{3b}$; R$_5$; X; n; R'$_4$, R''$_4$ have respectively the following meanings:

H;-;-; 2-Cl-Phe; H; H; H; O; 1; H; Phe;
H;-;-; 2-Cl-Phe; H; H; H; O; 2; Me; Me;
H;-;-; 2-Cl-Phe; H; H; —CH$_2$CH═C(Me)$_2$; O; 1; H; Phe;
H;-;-; 2-Cl-Phe; H; H; aminohexylcarbonyl; O; 1; H; Phe;
H;-;-; 2-Cl-Phe; H; H; aminopentylcarbonyl; O; 1; H; Phe;
H;-;-; 2-Cl-Phe; H; H; indolylmethylcarbonyl; O; 1; H; Phe;
H;-;-; 2-Cl-Phe; H; H; aminobutylcarbonyl; O; 1; H; Phe;
H;-;-; 2-Cl-Phe; H; H; propylcarbonyl; O; 1; H; Phe;
H;-;-; 2-Cl-Phe; H; H; cyclopentyl-methylcarbonyl; O; 1; H; Phe;
H;-;-; 2-Cl-Phe; H; H; phenyl-propylcarbonyl; O; 1; H; Phe;
H;-;-; 2-Cl-Phe; H; H; phenylethylcarbonyl; O; 1; H; Phe;
H;-;-; 2-Cl-Phe; H; H; 4-(L-alanoyloxymethyl)benzyl carbonyl; 0; 1I; H Phe;
H;-;-; 2-Cl-Phe; H; H; 4-aminomethyl-phenylcarbonyl; O; 1; H; Phe;
H;-;-; Phe; H; H; NH$_2$—CH$_2$—C(O)—NH—CH$_2$—C(O)—NH—CH$_2$—C(O)—; O; 2; Me; Me;
H;-;-; neopentyl; H; H; aminohexylcarbonyl; O; 1; H; Phe;
H;-;-; isobutyl; H; H; aminohexylcarbonyl; O; 1; H; Phe;
R'$_1$—NH—C(Y)—; 2-NO$_2$-4-MeO-Phe; S; 2-Cl-Phe; H; H; H; O; 4; H; H;
R'$_1$—NH—C(Y)—; 2-NO$_2$-4-MeO-Phe; S; 2-Cl-Phe; H; H; —CH$_2$CH═C(Me)$_2$; O; 1; H; Phe;
R'$_1$—NH—C(Y)—; 2-NO$_2$-4-MeO-Phe; S; 2-Cl-Phe; H; H; aminohexylcarbonyl; O; 1; H; Phe;
R'$_1$—NH—C(Y)—; 2-NO$_2$-4-MeO-Phe; S; 2-Cl-Phe; H; H; propylcarbonyl; O; 1; H; Phe;
R'$_1$—NH—C(Y)—; 2-NO$_2$-4-MeO-Phe; S; 2-Cl-Phe; H; H; cyclopentyl-methylcarbonyl; O; 1; H; Phe;
R'$_1$—NH—C(Y)—; 2-NO$_2$-4-MeO-Phe; S; 2-Cl-Phe; H; H; phenyl-propylcarbonyl; O; 1; H; Phe;
R'$_1$—NH—C(Y)—; 2-NO$_2$-4-MeO-Phe; S; 2-Cl-Phe; H; H; phenylethylcarbonyl; O; 1; H; Phe;
R'$_1$—NH—C(Y)—; 2-NO$_2$-4-MeO-Phe; S; 2-Cl-Phe; H; H; aminobutylcarbonyl; O; 1; H; Phe.

9. A process for the preparation of a compound of claim 1 wherein A—B is —C═N—, R$_1$ is hydrogen and R$_{3a}$ is hydrogen or alkyl of 1 to 6 carbon atoms comprising reacting a compound of the formula

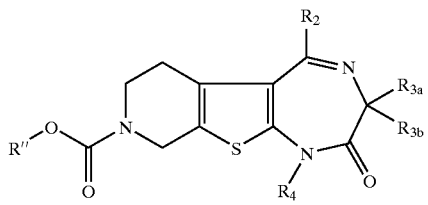
(1)

wherein $R_2$, $R_{3b}$ have the meaning of claim 1, $R_{3a}$ has the meaning above and R" is alkyl of 1 to 6 carbon atoms or lower aralkyl, with a compound $R_4Z$ in which $R_4$ has the meaning of claim 1 and Z is a parting group in the presence of a strong base, to obtain a compound of the formula

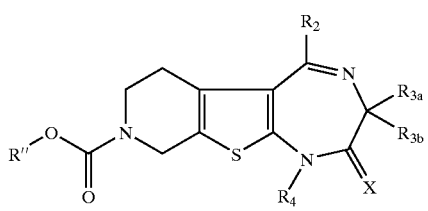
(2)

wherein X is oxygen, and reacting the latter with a thiation reagent to obtain compound (2) in which X is sulfur, and reacting a compound (2) in which X is oxygen or sulfur to a deprotection reaction of the carbamate to obtain the desired product.

10. A process for the preparation of compounds of claim 1 wherein A—B is —C=N—, $R_1$ is hydrogen and $R_{3a}$ is hydroxy comprising oxidizing a compound of the formula

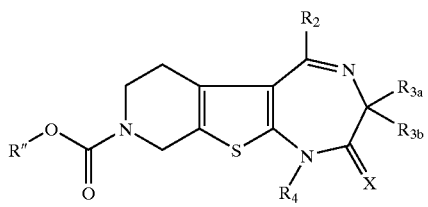
(2)

in an inert solvent to obtain a compound of the formula

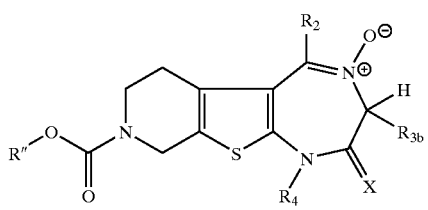
(3)

wherein $R_2$, $R_{3b}$, $R_4$ and X have the meaning of claim 1 and R" is alkyl of 1 to 6 carbon atoms or lower aralkyl, reacting the said compound with acetic anhydride to obtain a compound of the formula

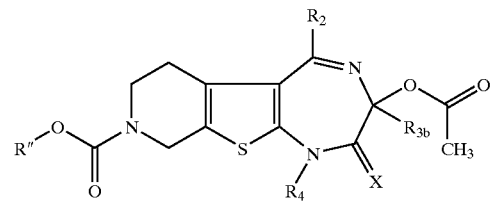
(4)

in which $R_2$, $R_{3b}$, $R_4$, R" and X have the meaning indicated above, saponifying the compound of the formula

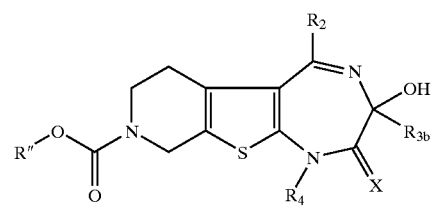
(5)

in which $R_2$, $R_{3b}$, $R_4$, R" and X have the meaning indicated above, and subjecting the compound to a deprotection reaction of the carbamate to obtain the corresponding compound of formula (I) in which $R_1$ is H and $R_{3a}$ is hydroxy.

11. A process for the preparation of a compound of claim 1 wherein A—B is —C=N—, $R_1$ is hydrogen and $R_{3a}$ is —OC(O)—R'$_{3a}$ comprising reacting a compound of the formula

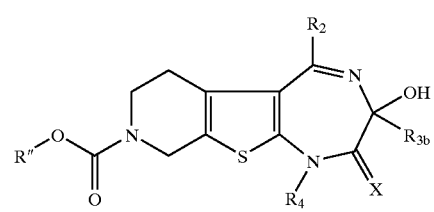
(5)

with R'$_{3a}$ C(O)OH in which R'$_{3a}$, $R_{3b}$, $R_2$ and $R_4$ have the meaning of claim 1, and R" is alkyl of 1 to 6 carbon atoms or lower aralkyl, X is O or S to obtain a compound of the formula

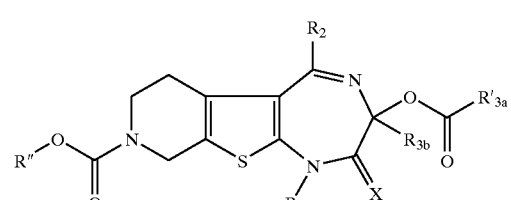
(6)

in which $R_2$, R'$_{3a}$, $R_{3b}$, $R_4$, R" and X have the meaning indicated above, and subjecting the compound to a deprotection reagent of the carbamate to obtain the corresponding compound of formula (I) in which $R_1$ is H and $R_{3a}$ is —OC(O)—R'$_{3a}$.

12. A process for the preparation of a compound of claim 1 wherein A—B is —C—N($R_5$)—, $R_1$ and $R_5$ are hydrogen and $R_{3a}$ is hydrogen or alkyl of 1 to 6 carbon atoms comprising reacting a gentle reducing agent in acid medium with a compound of the formula

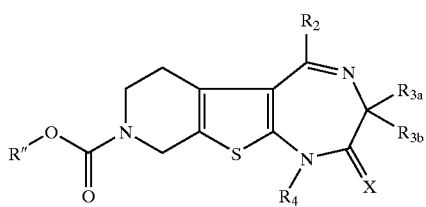
(2)

to obtain a compound of the formula

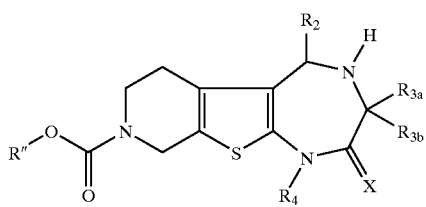
(8)

in which $R_2$, $R_{3b}$, $R_4$ and X have the meaning of claim 1, $R_{3a}$ has the meaning indicated above and R" is alkyl of 1 to 6 carbon atoms or lower aralkyl and subjecting the compound to a deprotection reaction of the carbamate to obtain the desired product (I) in which $R_1$ is hydrogen.

13. A process for the preparation of a compound of claim 1 wherein A—B is —C—N($R_5$)—, $R_1$ is hydrogen, $R_{3a}$ is hydrogen or alkyl of 1 to 6 carbon atoms and $R_5$ is alkenyl of up to 6 carbon atoms comprising reacting a compound of the formula

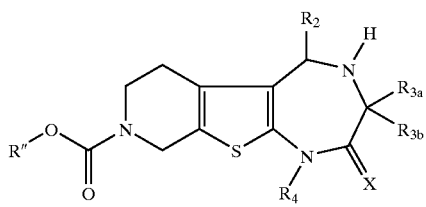
(8)

with a compound of the formula Z'—$R_5$, $R_5$ has the meaning indicated above and Z' is a parting group, in the presence of a strong mineral base in an inert solvent, to obtain a compound of the formula

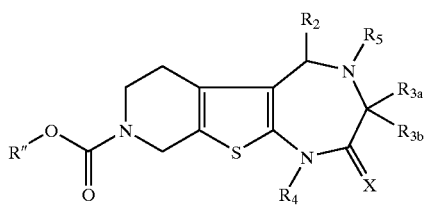
(9)

in which $R_2$, $R_{3b}$, $R_4$ and X have the meaning of claim 1, $R_{3a}$ and $R_5$ have the meaning indicated above and R" is alkyl of 1 to 6 carbon atoms and aralkyl and the compound is subjected to a deprotection reaction of the carbamate to obtain the desired product (I) in which $R_1$ is hydrogen.

14. A process for the preparation of a compound of claim 1 wherein A—B is —C—N($R_5$)—, $R_1$ is hydrogen, $R_{3a}$ is hydrogen or alkyl of 1 to 6 carbon atoms and $R_5$ is —C(O)—(CH$_2$)$_p$—R'$_5$, comprising reacting a compound of the formula

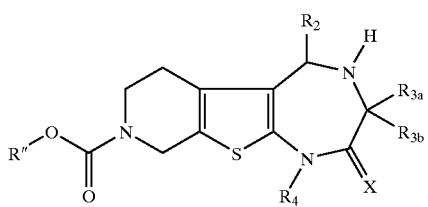
(8)

with an acid of the formula R'$_5$—(CH$_2$)$_p$—C(O)OH in which R'$_5$ and p have the meaning indicated in claim 1 to obtain a compound of the formula (10)

in which $R_2$, $R_{3b}$, $R_4$ and X have the meaning of claim 1, $R_{3a}$, R'$_5$ and p have the meaning indicated above and R" is alkyl of 1 to 6 carbon atoms or lower aralkyl and the compound is subjected to a deprotection reaction of the carbamate to obtain the desired product (I) in which $R_1$ is hydrogen.

15. A process for the preparation of a compound of claim 1 wherein $R_1$ is R'$_1$—NH—C(Y)—, comprising reacting a compound of formula (I) in which $R_1$ is hydrogen, with a compound of the formula $$R'_1-N=C=Y \qquad (7)$$

in which R'$_1$ and Y have the meaning indicated in claim 1, to obtain a compound of formula I.

16. A compound of the formula (2)

wherein R" is alkyl of 1 to 6 carbon atoms or lower aralkyl, $R_2$, $R_{3b}$ and $R_4$ are defined as in claim 1, $R_{3a}$ is hydrogen and X is sulfur or oxygen.

17. A composition for treating a disease selected from the group consisting of acromegalia, hypophyseal adenomas and endocrinic gastroenteropancreatic tumors comprising an effective amount of a compound of claim 1 and an inert pharmaceutical carrier.

18. A method of treating a disease selected from the group consisting of acromegalia, hypophyseal adenomas and endocrinic gastroenteropancreatic tumors in warm-blooded animals comprising administering to warm-blooded animals in need thereof an effective amount of at least one compound of claim 1 to treat said disease.

* * * * *